(12) United States Patent
Fell et al.

(10) Patent No.: US 6,888,044 B2
(45) Date of Patent: May 3, 2005

(54) HIGH CAPACITY ABSORBENT STRUCTURE AND METHOD FOR PRODUCING SAME

(75) Inventors: David A. Fell, Neenah, WI (US); Cornelius Bosselaar, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 224 days.

(21) Appl. No.: 10/327,836

(22) Filed: Dec. 23, 2002

(65) Prior Publication Data

US 2004/0122394 A1 Jun. 24, 2004

(51) Int. Cl.[7] .................................................. A61F 13/15
(52) U.S. Cl. ...................... 604/367; 604/366; 604/372; 604/365
(58) Field of Search ................................. 604/366, 367, 604/370, 365, 372; 442/374, 381, 396, 398; 428/144, 172, 212

(56) References Cited

U.S. PATENT DOCUMENTS

| | | | |
|---|---|---|---|
| 2,295,016 A | 9/1942 | Scribner | |
| 2,295,439 A | 9/1942 | Voigtman | |
| 2,468,876 A | 5/1949 | Hermanson | |
| 2,582,344 A | 1/1952 | Milton | |
| 2,772,678 A | 12/1956 | Leupold | |
| 2,833,283 A | 5/1958 | Spahr et al. | |
| 2,960,089 A | 11/1960 | Harwood et al. | |
| 3,067,747 A | 12/1962 | Wolterding et al. | |
| 3,078,849 A | 2/1963 | Morse | |
| 3,124,135 A | 3/1964 | Olson | |
| 3,143,113 A | 8/1964 | Mills | |
| 3,343,543 A | 9/1967 | Glasman | |
| 3,375,827 A | 4/1968 | Bletzinger et al. | |
| 3,403,681 A | 10/1968 | Hoey et al. | |
| 3,441,023 A | 4/1969 | Rijssenbeek | |
| 3,463,154 A | 8/1969 | Hendricks | |
| 3,477,433 A | 11/1969 | Dillon | |
| 3,525,337 A | 8/1970 | Simons et al. | |
| 3,563,242 A | 2/1971 | Hedstrom et al. | |
| 3,593,717 A | 7/1971 | Jones, Sr. | |
| 3,595,235 A | 7/1971 | Jespersen | |
| 3,654,929 A | 4/1972 | Nilsson et al. | |
| 3,658,062 A | 4/1972 | Kapur | |
| 3,658,064 A | 4/1972 | Pociluyko | |
| 3,667,468 A | 6/1972 | Nystrand et al. | |
| 3,699,966 A | 10/1972 | Chapuis | |
| 3,746,592 A | 7/1973 | Nystrand et al. | |
| 3,749,627 A | 7/1973 | Jones, Sr. | |
| 3,759,262 A | 9/1973 | Jones, Sr. | |
| 3,769,978 A | 11/1973 | DeNight et al. | |
| 3,771,525 A | 11/1973 | Chapuis | |
| 3,825,006 A | 7/1974 | Ralph | |

(Continued)

FOREIGN PATENT DOCUMENTS

| | | |
|---|---|---|
| DE | 4013015 A1 | 4/1990 |
| EP | 0139351 A2 | 2/1985 |
| EP | 0 260 108 A1 | 3/1988 |

(Continued)

OTHER PUBLICATIONS

Melius et al., U.S. Appl. No. 08/773,716, filed Oct. 29, 1993, entitled, "Absorbent Composite", pp. 1–54.

(Continued)

*Primary Examiner*—Jacqueline F. Stephens
(74) *Attorney, Agent, or Firm*—Brinks Hofer Gilson & Lione; G. Peter Nichols

(57) ABSTRACT

An absorbent core for use in an absorbent article such as a diaper, training pant, feminine hygiene product, or an incontinence product includes a stabilized first absorbent layer and a second absorbent layer that contains a superabsorbent and absorbent fibers treated with a non-fugitive densification agent.

44 Claims, 5 Drawing Sheets

U.S. PATENT DOCUMENTS

| | | |
|---|---|---|
| 3,865,112 A | 2/1975 | Roeder |
| 3,886,941 A | 6/1975 | Duane et al. |
| 3,897,784 A | 8/1975 | Fitzgerald |
| 3,926,189 A | 12/1975 | Taylor |
| 3,932,322 A | 1/1976 | Duchane |
| 3,939,838 A | 2/1976 | Fujinami et al. |
| 3,954,107 A | 5/1976 | Chesky et al. |
| 4,019,517 A | 4/1977 | Glassman |
| 4,022,210 A | 5/1977 | Glassman |
| 4,029,101 A | 6/1977 | Chesky et al. |
| 4,036,234 A | 7/1977 | Ishizuka |
| 4,057,061 A | 11/1977 | Ishikawa et al. |
| 4,072,150 A | 2/1978 | Glassman |
| 4,079,739 A | 3/1978 | Whitehead |
| 4,217,901 A | 8/1980 | Bradstreet et al. |
| 4,235,982 A | 11/1980 | Maslanka et al. |
| D259,211 S | 5/1981 | Larko |
| 4,265,245 A | 5/1981 | Glassman |
| 4,276,338 A | 6/1981 | Ludwa et al. |
| 4,315,507 A | 2/1982 | Whitehead et al. |
| 4,357,939 A | 11/1982 | Jackson et al. |
| 4,372,312 A | 2/1983 | Fendler et al. |
| D268,364 S | 3/1983 | Larko |
| 4,397,644 A | 8/1983 | Matthews et al. |
| 4,496,360 A | 1/1985 | Joffe et al. |
| 4,501,587 A | 2/1985 | Enloe |
| 4,531,945 A | 7/1985 | Allison |
| 4,551,142 A | 11/1985 | Kopolow |
| 4,568,341 A | 2/1986 | Mitchell |
| 4,573,986 A | 3/1986 | Minetola et al. |
| 4,573,989 A | 3/1986 | Karami et al. |
| 4,578,073 A | 3/1986 | Dysart et al. |
| 4,592,751 A | 6/1986 | Gegelys |
| D284,891 S | 7/1986 | Larko et al. |
| 4,597,760 A | 7/1986 | Buell |
| 4,597,761 A | 7/1986 | Buell |
| 4,627,848 A | 12/1986 | Lassen et al. |
| 4,631,062 A | 12/1986 | Lassen et al. |
| D287,881 S | 1/1987 | Ternstrom |
| 4,643,726 A | 2/1987 | Gegelys |
| 4,650,483 A | 3/1987 | Joffee |
| 4,676,786 A | 6/1987 | Nishino |
| 4,731,071 A | 3/1988 | Pigneul |
| 4,741,835 A | 5/1988 | Jacques et al. |
| 4,781,962 A | 11/1988 | Zamarripa et al. |
| 4,798,601 A | 1/1989 | Shirose et al. |
| 4,798,603 A | 1/1989 | Meyer et al. |
| 4,801,494 A | 1/1989 | Datta et al. |
| 4,806,408 A | 2/1989 | Pierre et al. |
| 4,822,668 A | 4/1989 | Tanaka et al. |
| 4,834,737 A | 5/1989 | Khan |
| 4,846,824 A | 7/1989 | Lassen et al. |
| D302,854 S | 8/1989 | Minot |
| 4,892,534 A | 1/1990 | Datta et al. |
| 4,892,598 A | 1/1990 | Stevens et al. |
| 4,908,026 A | 3/1990 | Sukiennik et al. |
| 4,923,454 A | 5/1990 | Seymour et al. |
| 4,938,756 A | 7/1990 | Salek |
| 4,950,264 A | 8/1990 | Osborn, III |
| 4,963,139 A | 10/1990 | Dabroski |
| 4,964,857 A | 10/1990 | Osborn |
| 4,973,325 A | 11/1990 | Sherrod et al. |
| 5,009,653 A | 4/1991 | Osborn, III |
| 5,019,070 A | 5/1991 | Ruben |
| 5,037,412 A | 8/1991 | Tanzer et al. |
| 5,043,206 A | 8/1991 | Ternstrom |
| 5,048,347 A | 9/1991 | Knowles |
| 5,090,249 A | 2/1992 | Bielewicz |
| 5,128,082 A | 7/1992 | Makoui |
| 5,135,521 A | 8/1992 | Luceri et al. |
| 5,160,331 A | 11/1992 | Forester et al. |
| 5,207,662 A | 5/1993 | James |
| 5,217,447 A | 6/1993 | Gagnon |
| 5,236,428 A | 8/1993 | Zajaczkowski |
| D340,977 S | 11/1993 | Provencher |
| D345,014 S | 3/1994 | Huffman |
| 5,300,055 A | 4/1994 | Buell |
| D348,102 S | 6/1994 | Gegelys et al. |
| D349,159 S | 7/1994 | Huffman |
| D350,196 S | 8/1994 | Huffman |
| D350,197 S | 8/1994 | Huffman |
| D350,198 S | 8/1994 | Huffman |
| 5,342,340 A | 8/1994 | Kichefski et al. |
| 5,360,422 A | 11/1994 | Brownlee et al. |
| 5,364,382 A | 11/1994 | Latimer et al. |
| D353,670 S | 12/1994 | Huffman |
| 5,378,528 A | 1/1995 | Makoui |
| 5,387,208 A | 2/1995 | Ashton et al. |
| 5,401,266 A | 3/1995 | Runeman et al. |
| 5,403,303 A | 4/1995 | Beplate |
| 5,405,342 A | 4/1995 | Roessler et al. |
| 5,409,476 A | 4/1995 | Coates |
| 5,411,497 A | 5/1995 | Tanzer et al. |
| 5,423,787 A | 6/1995 | Kjellberg |
| 5,425,725 A | 6/1995 | Tanzer et al. |
| 5,433,715 A | 7/1995 | Tanzer et al. |
| 5,437,653 A | 8/1995 | Gilman et al. |
| 5,454,800 A | 10/1995 | Hirt et al. |
| 5,458,591 A | 10/1995 | Roessler et al. |
| 5,460,624 A | 10/1995 | Ahr et al. |
| 5,466,232 A | 11/1995 | Cadieux et al. |
| H1511 H | 12/1995 | Chappell et al. |
| 5,476,457 A | 12/1995 | Roessler et al. |
| 5,509,915 A | 4/1996 | Hanson et al. |
| 5,514,120 A | 5/1996 | Johnston et al. |
| 5,518,585 A | 5/1996 | Huth et al. |
| 5,520,673 A | 5/1996 | Yarbrough et al. |
| 5,556,393 A | 9/1996 | Ronnbert |
| 5,593,399 A | 1/1997 | Tanzer et al. |
| 5,601,542 A | 2/1997 | Melius et al. |
| D378,407 S | 3/1997 | Bunton |
| 5,609,588 A | 3/1997 | DiPalma et al. |
| 5,613,959 A | 3/1997 | Roessler et al. |
| 5,613,962 A | 3/1997 | Kenmochi et al. |
| 5,643,240 A | 7/1997 | Jackson et al. |
| 5,647,862 A | 7/1997 | Osborn, III et al. |
| D384,150 S | 9/1997 | Gray et al. |
| 5,695,488 A | 12/1997 | Sosalla |
| D392,737 S | 3/1998 | Byer |
| 5,797,894 A | 8/1998 | Cadieux et al. |
| D398,055 S | 9/1998 | Burden |
| 5,803,920 A | 9/1998 | Gilman |
| 5,846,230 A | 12/1998 | Osborn, III et al. |
| D411,007 S | 6/1999 | Peck |
| 5,925,026 A | 7/1999 | Arteman et al. |
| 5,938,650 A | 8/1999 | Baer et al. |
| 5,980,500 A | 11/1999 | Shimizu et al. |
| 5,994,615 A | 11/1999 | Dodge, II et al. |
| 6,060,638 A | 5/2000 | Paul et al. |
| 6,229,061 B1 | 5/2001 | Dragoo et al. |

FOREIGN PATENT DOCUMENTS

| | | |
|---|---|---|
| EP | 0319314 A2 | 6/1989 |
| EP | 0 416 427 A1 | 3/1991 |
| EP | 0549988 A1 | 7/1993 |
| EP | 0572033 A2 | 12/1993 |
| EP | 0627178 A1 | 12/1994 |
| EP | 0667136 A1 | 8/1995 |
| EP | 0763353 A2 | 3/1997 |
| EP | 0945110 A2 | 3/1999 |
| EP | 1005847 A2 | 6/2000 |

| | | | | | |
|---|---|---|---|---|---|
| GB | 1333081 | 10/1973 | WO | WO 02/077041 A2 | 10/2002 |
| GB | 1 462 441 | 1/1977 | WO | WO 02/077042 A2 | 10/2002 |
| JP | 60220137 | 11/1985 | WO | WO 02/077365 A1 | 10/2002 |
| JP | 04046915 | 2/1992 | | | |
| JP | 04309510 | 11/1992 | | | |
| WO | WO 91/09583 | 7/1991 | | | |
| WO | WO 91/16871 | 11/1991 | | | |
| WO | WO 94/26221 | 11/1994 | | | |
| WO | WO 95/10996 | 4/1995 | | | |
| WO | WO 96/12459 | 5/1996 | | | |
| WO | WO 96/29037 | 9/1996 | | | |
| WO | WO 97/06765 | 2/1997 | | | |
| WO | WO 00/37011 | 6/2000 | | | |
| WO | WO 00/45762 | 8/2000 | | | |
| WO | WO 02/077040 A2 | 10/2002 | | | |

OTHER PUBLICATIONS

Gilman, U.S. Appl. No. 09/146,458, filed on Sep. 1, 1998, entitled, Thin Absorbent Article, pp. 1–31.

Sherrod et al., U.S. Appl. No. 09/825,609, filed on Apr. 3, 2001, entitled, "Absorbent Insert for Use With an Outer Absorbent Garment", pp. 1–20.

DiPalma et al., U.S. Appl. No. 10/330,417, filed Dec. 27, 2002, entitled, "Thin Curved Elasticized Absorbent Article with Absorbent Concentration Profile", pp.

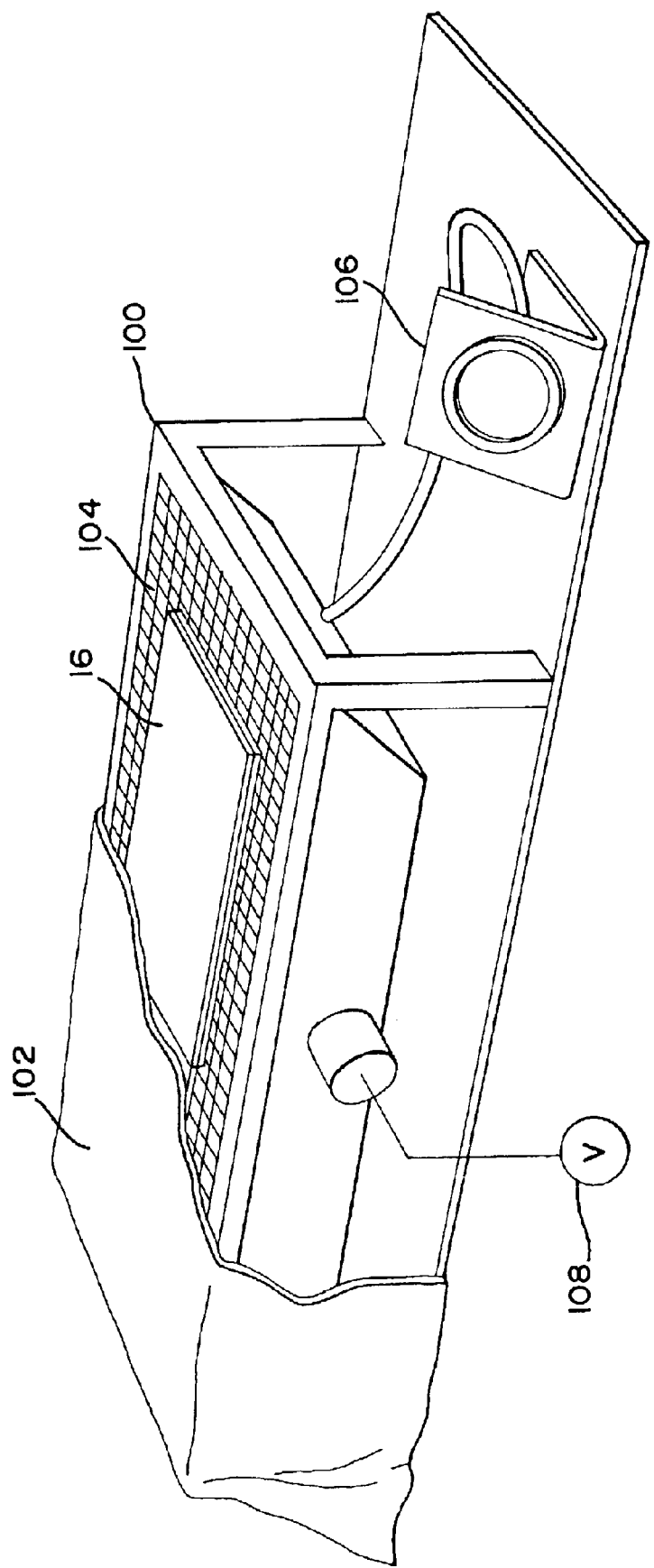

HIGH CAPACITY ABSORBENT STRUCTURE AND METHOD FOR PRODUCING SAME

BACKGROUND OF THE INVENTION

The present invention relates to a thin, high capacity absorbent core having a suitable level of stiffness for use in absorbent articles.

Disposable absorbent articles such as catamenial pads, sanitary napkins, pantyliners, adult incontinence pads and garments, diapers, and children's training pants are designed to be worn adjacent to the wearer's body to absorb body fluids such as menses, blood, urine and other bodily excretions. Users of absorbent articles include menstruating women, infants, children undergoing toilet training, and urine and bowel incontinent adults, among others. This broad user base with varying absorbency requirements has resulted in development of a broad range of commercial products to meet consumer absorbency needs.

Incontinence users experience important differences from menstruating women and the use of commercially available feminine care products may not satisfy their specific needs. Most incontinence users (adults, infants, and toilet training children, for example) require a product that can absorb and retain urine over an extended period of time. Since feminine care products are specifically designed to absorb and retain menses, many do not contain superabsorbents. Superabsorbents are capable of retaining large quantities of body fluid, such as urine, but it is known that they can impede the flow of menses. Without the presence of superabsorbents, many feminine care products do not have the fluid retention capacity needed by incontinence users. The presence of superabsorbents in incontinence products allows the liquid urine to be locked away so the product feels dry to the wearer. Many incontinence users tend to expel only a few drops of urine at a time and therefore they tend to wear their products over a longer time period. Others, including infants, toilet training children, and many incontinent adults can expel large quantities of urine ranging up to several hundred grams per urination and accordingly require substantial absorbent capacity in their absorbent garment. Another reason many adult incontinence users wear pantyliners or ultra thin catamenial pads for incontinence is that most incontinence products are thick and bulky rather than being thin and discreet. Incontinence users have a strong psychological reason for not wanting other people to know that they suffer from incontinence. There is, therefore, a need for thinner incontinence products that can provide a wide range of absorbent capacity to meet the wearer's specific needs.

Because of the above concerns, there is a need to produce a relatively inexpensive, thin incontinence pad, incontinence garment, or pantyliner, having a thickness of less than about 10 millimeters, desirably less than about 7 to about 8 millimeters and more desirably less than about 5 millimeters, which can absorb and retain from between about 20 grams to about 1200 grams of urine, or more.

Now, a relatively inexpensive, thin absorbent article has been invented that can do just that. This absorbent article contains an absorbent core formed from two or more layers of material, at least one of which contains a superabsorbent.

SUMMARY OF THE INVENTION

Briefly, this invention relates to an absorbent core formed from two or more layers for use in an absorbent article. Non limiting examples of absorbent articles that may use the absorbent core of the present invention include an incontinence pad, pantyliner, diaper, children's training pant, adult incontinence garment, arm pads, bed pads, milk pads, and other articles that are intended to absorb fluids. The absorbent core can be formed from two or more layers of material for providing protection against involuntary loss of body fluids. The absorbent article may include a liquid permeable bodyside liner, a liquid-impermeable baffle, and an absorbent core, which is positioned between the liner and the baffle. Advantageously, articles formed with the absorbent core according to the present invention better resist deformation and maintain their integrity during use.

The absorbent core includes at least a first absorbent layer and a second absorbent layer, at least one of which contains a superabsorbent. The first absorbent includes a stabilized material that may contain superabsorbent. The second absorbent includes a superabsorbent and absorbent fibers that may be treated with a non-fugitive densification agent. The second absorbent may have a density greater than the first absorbent layer.

As used in the following specification and appended claims, the phrase "non-fugitive densification agent" refers to any agent that has a volatility less than water and/or that forms a hydrogen bond with the fibers or has an affinity for the fibers and provides an ability to decrease the force required to densify the fibrous mass or absorbent containing the fibers.

Unless otherwise specifically noted, all percentages referred to in the following specification and appended claims refer to a percent by weight.

The general object of this invention is to provide an absorbent article that has an absorbent core constructed from two or more layers of material for containing body fluid expelled from a human body. A more specific object of this invention is to provide a thin incontinence pad or pantyliner for absorbing and retaining urine and a method of forming the product. Another object of the invention is to provide an absorbent core that better resists deformation and maintains its integrity and shape in use.

Another object of this invention is to provide an absorbent article that has a thickness of less than about 10 millimeters, desirably less than about 7 to about 8 millimeters, and more desirably less than about 5 millimeters.

A further object of this invention is to provide a thin absorbent article that uses an absorbent core formed from two or more layers of material, at least one of which contains a superabsorbent.

Another object of this invention is to provide a method of forming the absorbent core. Related to this object is a method of making a thin high capacity absorbent core that minimizes damage to the superabsorbent during the manufacturing process.

Still further, an object of this invention is to provide a reasonably priced, thin absorbent article that is easy to manufacture.

Other objects and advantages of the present invention will become more apparent to those skilled in the art in view of the following description and the accompanying drawings

BRIEF DESCRIPTION OF THE DRAWINGS

FIG. 9 is an illustration of the equipment used to determine the retention capacity of an absorbent structure.

DESCRIPTION OF THE INVENTION

Figure 1:
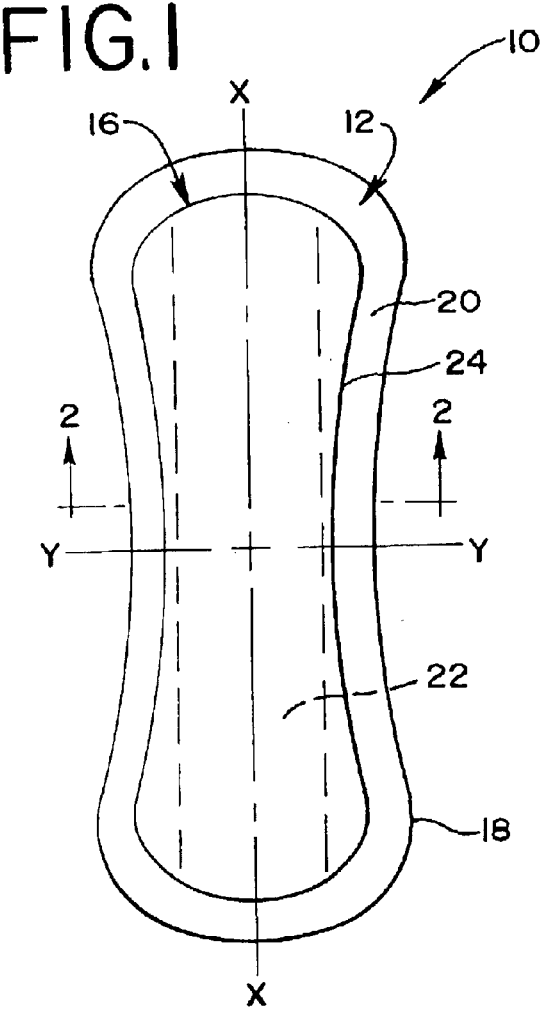
FIG. 1 is a top view of an absorbent article such as a thin incontinence pad or a pantyliner designed to absorb and retain urine and containing an absorbent core according to the present invention.
Figure 2:
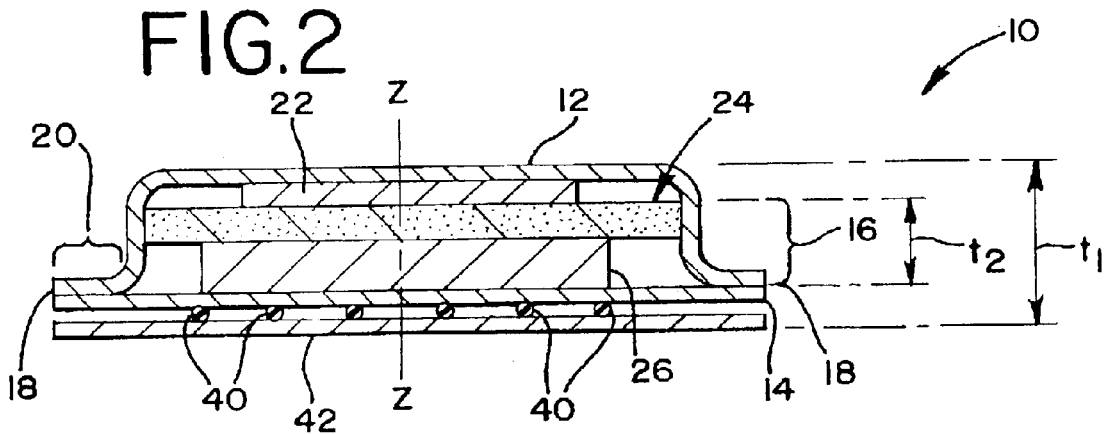
FIG. 2 is a cross-sectional view of the absorbent article shown in FIG. 1 taken along line 2—2.

Referring now to the drawings and initially to FIG. 1, an absorbent article 10 is shown which is depicted as a thin incontinence pad or pantyliner. The absorbent article 10 is designed to be secured to an inside surface of a person's undergarment by a garment adhesive and is designed to absorb and retain urine that is involuntarily expelled from the body. The absorbent article 10 is an elongated product having a central longitudinal axis x—x and a central transverse axis y—y. The absorbent article also has a vertical axis z—z, as shown in FIG. 2. The absorbent article 10 is relatively thin, less than about 10 mm thick. Alternatively, for absorbent articles that are more garment-like than pads, such as diapers, children's training pants, and adult incontinence pants, the article can be pulled on like normal underwear or placed on the body and then secured with fasteners such as tape and hook and loop material commonly used for disposable diapers.

By "thin" it is meant that the absorbent article 10 has a thickness of less than about 10 millimeters. Desirably, the absorbent article 10 has a thickness of less than about 7 to about 8 millimeters, and more desirably, the absorbent article 10 has a thickness of less than about 5 millimeters.

The absorbent article 10 has a fluid retention capacity capable of absorbing from between about 20 grams to about 1200 grams of urine, or more. The required fluid retention capacity is product and consumer dependent and can be modified according to the present invention to meet the product and consumer requirements.

The absorbent article 10 includes a liquid permeable liner or cover 12, a liquid-impermeable baffle 14, and an absorbent core 16 positioned and enclosed between the liner 12 and the baffle 14.

The bodyside liner 12 is designed to be in contact with the wearer's body. The bodyside liner 12 can be constructed of a woven, perforated film, or nonwoven material that is easily penetrated by body fluid, especially urine. The liner 12 can also be formed from either natural or synthetic fibers. Suitable materials include bonded-carded webs of polyester, polypropylene, polyethylene, nylon or other heat-bondable fibers. Other polyolefins, such as copolymers of polypropylene and polyethylene, linear low-density polyethylene, finely perforated film webs and net materials, also work well. A suitable material is a soft, wettable polypropylene homopolymer spunbond having a basis weight of from between about 13 grams per square meter (gsm) to about 27 gsm. Another suitable material is an apertured thermoplastic film. Still another material for the bodyside liner 12 is a spunbond web of bicomponent polypropylene/polyethylene side by side or in a sheath/core configuration. The spunbond web can contain from between about one percent (1%) to about six percent (6%) of titanium dioxide pigment to give it a clean, white appearance. A desirable polypropylene web has a basis weight of from between about 13 to about 40 grams per square meter (gsm). An optimum basis weight is from between about 15 gsm to about 25 gsm. The thickness of the bodyside liner 12 can range from between 0.1 mm to about 1.0 mm.

It should be noted the bodyside liner 12 could be coated, sprayed or otherwise treated with a surfactant to make it hydrophilic. By "hydrophilic" it is meant that the bodyside liner 12 will have a strong affinity for water and a contact angle of less than 90 degrees. The body side liner 12 may also be inherently hydrophilic. When the bodyside liner 12 is formed from a hydrophilic material, it will allow the body fluid to pass quickly therethrough. The bodyside liner 12 can also be embossed to improve the aesthetic appearance of the absorbent article 10.

The liquid permeable liner 12 and the liquid-impermeable baffle (or backsheet) 14 cooperate to enclose and retain the absorbent core 16. The liner 12 and the baffle 14 can be cut, sized, and shaped to have a coterminous outer edge 18. When this is done, the liner 12 and the baffle 14 can be bonded in face to face contact to form an absorbent article 10 having a peripheral seal or fringe 20. The peripheral fringe can be formed to have a width of about 5 millimeters.

The liner 12 and the baffle 14 can have any suitable shape. In general, however, each will have a shape generally in the form of a dogbone, hourglass, t-shape, or racetrack configuration. With a dog bone or hourglass configuration, the absorbent article 10 will have a narrow section located adjacent to the central transverse axis y—y that separates a pair of larger, end lobes. The end lobes can be sized and/or shaped differently, if desired. An absorbent article 10 having a dogbone or hourglass shape is more comfortable to wear than a generally rectangular shaped product. The absorbent article 10 can also be asymmetrical. The liner 12 and the baffle 14 can be bonded or sealed together about their periphery by a construction adhesive to form a unitary absorbent article 10. Alternatively, the liner 12 and the baffle 14 can be bonded together by heat, pressure, by a combination of heat and pressure, by ultrasonics, or other means to form a secure attachment.

The liquid-impermeable baffle 14 can be designed to permit the passage of air or vapor out of the absorbent article 10 while blocking the passage of body fluid, such as urine. The baffle 14 can be made from any material exhibiting these properties. The baffle 14 can also be constructed from a material that will block the passage of vapor as well as fluids, if desired. A good material for the baffle 14 is a micro-embossed, polymeric film, such as polyethylene or polypropylene. Bicomponent films can also be used. A suitable material is polyethylene film. The baffle 14 can also be formed as a laminate of film and a nonwoven such as a spunbond. In a particular embodiment, the baffle 14 will be comprised of a polyethylene film having a thickness in the range of from between about 0.1 mm to about 1.0 mm. The baffle 14 may be about 150 mm to about 320 mm long, and about 60 mm to about 120 mm wide. It is to be understood, however, that for garment-like products such as diapers, pull-on pants, adult briefs, bed pads and the like, the baffle 14 will have a size suitable to meet the needs of the product.

It is also possible to incorporate a surge layer 22. The purpose of a surge layer is to quickly take up and temporarily hold the urine until the absorbent core 16 has adequate time to absorb the urine. The surge layer can be formed from various materials. Two good materials from which the surge layer can be formed include a crimped bicomponent spunbond or from a bonded carded web. When a surge layer is used, it should be designed to have a basis weight from between about 20 gsm to about 120 gsm and a thickness ranging from between about 0.1 mm to about 5 mm. The following U.S. Patents teach surge layers: U.S. Pat. Nos. 5,364,382; 5,429,629; 5,486,166; and 5,490,846, the relevant portions of which are incorporated herein by reference.

Referring to FIG. 2, the absorbent article 10 has an absorbent core 16 that is positioned between the surge layer 22 and the liquid-impermeable baffle 14. If no surge layer 22 is present, the absorbent core 16 is positioned between the bodyside liner 12 and the liquid-impermeable baffle 14. The absorbent core 16 includes a first absorbent 24 and a second absorbent 26.

In one embodiment, as shown in FIG. 2, the first absorbent 24 is arranged close to the liner 12 and is positioned vertically above the second absorbent 26. For purposes of definition and orientation, the liner 12 is depicted in FIG. 2 as the "top" of the absorbent article 10 and the other components such as the first absorbent 24, the second absorbent 26, and the baffle 14 are positioned vertically "below" the liner 12. The first absorbent 24 may be in direct face to face contact with the second absorbent 26. In this regard, the first absorbent 24 can be adhered, for example, by an adhesive, to the second absorbent 26 to ensure intimate contact and better fluid transfer between them.

Even though the first and second absorbents, 24 and 26 respectively, may be in direct contact with one another, it is possible to place one or more layers of tissue or fabric between them. Some manufacturers like to wrap an absorbent containing superabsorbent particles to prevent the superabsorbent particles from escaping from the finished product. Accordingly, the first absorbent 24 and/or the second absorbent 26 may be wrapped in tissue or a fabric wrap such as a low basis weight spunbond/meltblown or spunbond/meltblown/spunbond composite.

Referring again to FIG. 1, the first absorbent 24 is depicted as having a shaped periphery in the form of a dog bone configuration. Other shapes, such as a rectangle, an hourglass shape, an oval shape, a trapezoid shape, or an asymmetrical shape formed about the longitudinal axis, etc. can also be used. A peripheral shape, wherein the first absorbent 24 is narrowest in the middle along the central transverse axis y—y, works well for it will be more comfortable to wear. A trapezoidal or tapered configuration works well for a male incontinent product.

The first absorbent 24 is a stabilized layer that includes absorbent fibers and may contain a superabsorbent material. The first absorbent 24 of the present invention advantageously can be presented as a stabilized absorbent layer. As used herein, the term "stabilized absorbent" refers to an absorbent structure or layer that includes binder agents or other materials added to a mixture of other absorbent materials, such as wood pulp fluff and superabsorbent material, when included, to provide an absorbent matrix that has a dry tensile strength of about 6 Newtons/5 cm of more and a wet tensil strength of about 2 Newtons/5 cm or more. It should be noted that the binder agents may be homogeneously added to the absorbent mixture, or they may be added to the absorbent mixture in a stratified configuration. The binder agents are then activated to bond the resultant absorbent matrix together in both a dry and a wet state. Some stabilized absorbent materials such as foams and coform (produced by Kimberly-Clark Corp. with offices in Roswell, Ga.) do not require a separate activation process to achieve the necessary tensile strength.

The first absorbent 24 may be constructed of any number of absorbent materials as are well known in the art. For example, the first absorbent layer may be provided by a layer of "airlaid", coform, meltblown fibers, bonded carded webs, tissue laminates, absorbent films, foams, a surge/airlaid composite and the like or combinations thereof. The first layer can also be provided by a stabilized wet laid material as described in PCT WO98/51251 with superabsorbent or without superabsorbent, as described in PCT WO 98/24392, the relevant portions of both are incorporated herein by reference.

In one embodiment, the first absorbent 24 may be provided as an airlaid pledget that can be a combination of hydrophilic fibers, high absorbency material, and binder material. As used herein, the term "airlaid" refers to the process of producing an absorbent material where unlike components are conveyed in an air-stream and homogenously mixed or provided in a stratified configuration and then bonded together. For example, this may include, but is not limited to, the mixture of pulp fibers, synthetic fibers, superabsorbent materials and binder material. The binder material is often, but not limited to, synthetic bicomponent binder fibers and/or latexes. There are a number of commercial processes available to produce airlaid absorbent structures. For example, airlaid processes are available from Danweb Corp. having offices in Risskov, Denmark, and from M&J Forming Technologies having offices in Horsens, Denmark.

An airlaid process provides uniformity of the mixture of raw materials and the ability to add synthetic fibers and/or binder agents to the mixture to stabilize the resultant absorbent. As a stabilizer, binders reduce the amount of wet collapse in the structure and maintain a lower density in the saturated state. That is, the binder assists the absorbent matrix in maintaining its integrity even under load or while saturated.

Various types of wettable, hydrophilic fibrous material can be used to provide the fiber material for the first absorbent 24. Examples of suitable fibers include naturally occurring organic fibers composed of intrinsically wettable material, such as cellulosic fibers; manmade fibers composed of cellulose or cellulose derivatives, such as rayon fibers; inorganic fibers composed of an inherently wettable material, such as glass fibers; synthetic fibers made from inherently wettable,thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material that has a suitable hydrophilic moiety and preferably is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be used.

Figure 3:
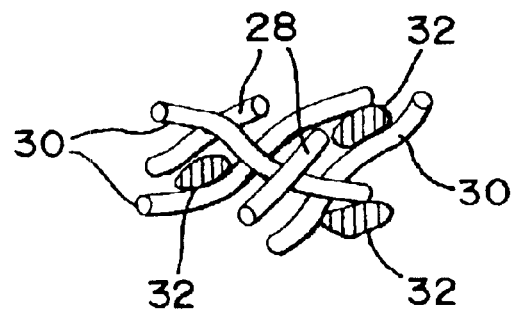
FIG. 3 is an enlarged view of the first absorbent shown in FIG. 2.

Referring to FIG. 3, the first absorbent 24 is shown as a blend of a first group of fibers 28, a binder 30, preferably in the form of a second group of fibers, and the optional superabsorbent 32, which is cured to form a stabilized, airlaid absorbent structure. The first group of fibers 28 can be cellulosic fibers, such as pulp fibers, that are short in length, have a high denier, and are hydrophilic. The first group of fibers 28 can be formed from 100% softwood fibers. Desirably, the first group of fibers 28 is southern pine Kraft pulp fibers. A suitable material to use for the first group of fibers 28 is Weyerhaeuser NB 416 pulp fibers, which is commercially available from Weyerhaeuser Company, Federal Way, Wash. Alternatively the first group of fibers can be manmade or synthetic fibers as previously described or the first group of fibers 28 may be a combination of these materials.

The binder portion of the first absorbent 24 can be a chemical coating or a wet adhesive application such as a latex that may be sprayed, foamed, or layered on the first absorbent. Desirably, the binder portion of the first absorbent 24 will consist of a second group of fibers 30. The second group of fibers 30 can be synthetic binder fibers. Synthetic binder fibers are commercially available from several suppliers. One such fiber is TREVIRA 255 2.2 decitex 3 mm Lot 1663 supplied by Trevira GmbH & Company KG having a mailing address of Max-Fischer-Strasse 11, 86397 Bobingen, Deutschland. Another supplier of binder fibers is Fibervisions a/s having a mailing address of Engdraget 22, Dk-6800 Varde, Denmark. A third supplier of binder fibers is KoSa having a mailing address of P.O. Box 4, Highway 70 West, Salisbury, N.C. 28145. Preferably, the second group of fibers 30 is bicomponent fibers having a polyester core surrounded by a polyethylene sheath. Alternatively, the second group of fibers 30 can be bicomponent fibers having a polypropylene core surrounded by a polyethylene sheath. The polyethylene sheath may be high density, low density, or linear low density polyethylene and may have an activating agent such as maleic anhydride incorporated into the polymer.

The fibers making up the second group of fibers 30 are longer in length and have a lower denier than the fibers making up the first group of fibers 28. The length of the fibers 30 can range from between about 3 mm to about 6 mm or more. A fiber length of 6 mm works well. The fibers 30 can have a denier of less than or equal to 2.0. The fibers 30 should be moisture insensitive and can be either crimped or non-crimped. Crimped fibers are preferred since they usually process better than non-crimped fibers.

As noted above, the first absorbent 24 may contain a superabsorbent 32. A superabsorbent is a material that is capable of absorbing at least 10 grams of water per gram of superabsorbent material. The superabsorbent 32 is preferably in the shape of small particles, although fibers, flakes or other forms of superabsorbents can also be used. A suitable superabsorbent 32 is FAVOR SXM 880. FAVOR SXM 880 is commercially available from Stockhausen, Inc., having an office located at 2408 Doyle Street Greensboro, N.C. 27406. Other similar types of superabsorbents, such as FAVOR SXM 9543 and FAVOR SXM 9145, which are commercially available from Stockhausen, can be used.

The superabsorbent 32 is present in the first absorbent 24 in a weight percent of from between about 0% to about 60%. The amount of superabsorbent 32 present in the first absorbent 24 depends on the composition of the second absorbent 26 and the ultimate function of the absorbent article 10. For example, it may be desirable to provide an absorbent article to achieve a high level of capacity. Accordingly, it may be desirable to provide superabsorbent 32 in the first absorbent 24. Alternatively, if the first absorbent 24 functions primarily to mask urine staining, facilitate liquid intake, and provide a stabilized layer at a minimum basis weight to lower the cost, then the first absorbent 24 need not contain a superabsorbent 32.

The individual components 28, 30, and 32 of the first absorbent 24 can be present in varying amounts. It has been found, however, that the following percentages work well in forming the thin absorbent article 10. The first group of fibers 28 can range from between about 30% to about 95% by weight, of the first absorbent 24. The second group of fibers 30 can range from between about 5% to about 40% by weight, of the first absorbent 24. The superabsorbent 32 can range from between about 0% to about 60% by weight, of the first absorbent 24. It has been found that forming a first absorbent 24 with about 50% to about 95% of the first group of fibers 28, about 5% to about 20% of the second group of fibers 30, and about 0% to about 40% of superabsorbent works well for absorbing and retaining urine.

The first group of fibers 28 should be present in the first absorbent 24 by a greater percent, by weight, than the second group of fibers 30. By using a greater percent of the first group of fibers 28 the overall cost of the first absorbent 24 can be reduced. The first group of fibers 28 also ensures that the absorbent article 10 has sufficient fluid absorbing capacity. Cellulosic fibers 28, such as pulp fibers, are generally less expensive than synthetic binder fibers 30. For good performance, the second group of fibers 30 should make up at least about 4% by weight of the first absorbent 24 to ensure that the first absorbent 24 has sufficient tensile strength in both a dry and wet state.

The first absorbent 24 also has a predetermined basis weight of from between about 60 gsm to about 800 gsm. Suitably, the first absorbent 24 has a basis weight of from between about 100 gsm to about 600 gsm. More suitably, the first absorbent 24 has a basis weight of from between about 100 gsm to about 200 gsm.

The first absorbent 24 is compressed in a substantially dry condition after heat curing at a temperature from about 140 to about 165° C. for a time of from between about 8 seconds to about 10 seconds to a density ranging from between about 0.05 g/cm$^3$ to about 0.4 g/cm$^3$. Desirably, the first absorbent 24 is compressed in a substantially dry condition to a density ranging from between about 0.06 g/cm$^3$ to about 0.22 g/cm$^3$. More desirably, the first absorbent 24 is compressed in a substantially dry condition to a density of at about 0.07 g/cm$^3$ to about 0.1 g/cm$^3$. This compression of the first absorbent 24 will assist in forming the thin absorbent article 10.

By providing a stabilized material with sufficient tensile strength, the stabilized material can be wound into rolls that can later be unwound and processed on converting equipment. In addition, sufficient tensile strength in a dry and wet state helps the absorbent article 10 to resist deformation and to increase its integrity during use. Sufficient tensile strength can be achieved by varying the content of the binder fiber or binder fiber components, adjusting the curing conditions, changing the specific density to which the fibers are compacted, as well as other ways known to one skilled in the art. It has been found that the first absorbent 24 should have a tensile strength of at least about 6 Newtons per 50 mm (N/50 mm). Desirably, the first absorbent 24 should have a tensile strength of at least about 18 N/50 mm. More desirably, the first absorbent 24 should have a tensile strength of at least about 25 N/50 mm.

The tensile strength of the material can be tested using a tester such as a Model 4201 Instron with Microcon II from Instron Corp. Canton, Mass. The machine is calibrated by placing a 100 gram weight in the center of the upper jaw, perpendicular to the jaw and hanging unobstructed. The tension cell used is a 5 kilogram electrically-calibrating self-identifying load cell. The weight is then displayed on the Microcon display window. The procedure is performed in a room with standard-condition atmosphere such as about a temperature of about 23° C. and a relative humidity of about 50 percent.

A rectangular sample about 5 cm by about 15 cm is weighed and pressure is applied to the sample to reach a desired density. The dry sample is then placed in the pneumatic action grips (jaws) with 1 inch (2.54 cm) by 3 inch (7.62 cm) rubber coated grip faces. The gauge length is 10 cm and the crosshead speed is 250 mm/minute. The crosshead speed is the rate at which the upper jaw moves upward pulling the sample until failure. The Tensile Strength value is the maximum load at failure, recorded in grams of force needed to permanently stretch or tear the sample. The tensile strength is evaluated for the material in both a dry condition and a 100 percent liquid saturated condition. The tensile strength for the material in a 100 percent liquid saturated condition is done by placing a dry sample in a container containing a sufficient excess of 0.9% saline solution for 20 minutes, after which the sample is placed in the jaws and the tensile strength is measured as described above.

Desirably, the first absorbent 24 is a stabilized airlaid absorbent to provide for integrity and tensile strength in the wet state and to improve liquid distribution. The first absorbent 24 according to the present invention has, in general, a dry strength of about 6 N/50 mm and a wet strength of at least about 2 N/50 mm.

The first absorbent 24 has any suitable thickness such that the overall thickness $t_1$ of the absorbent article 10 is less than about 10 millimeters. Desirably, the absorbent article 10 has a thickness of less than about 7 to about 8 millimeters, and more desirably, the absorbent article 10 has a thickness of less than about 5 millimeters. Put another way, the first absorbent 24 has any suitable thickness such that the thickness $t_2$ of the absorbent core 16 ranges from between about 2 mm to about 8 mm, desirably less than about 4 mm.

Figure 7:
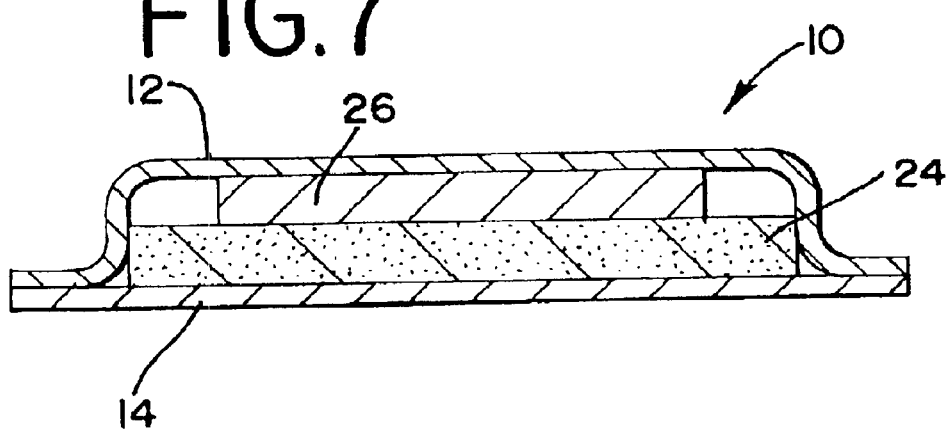
FIG. 7 is a cross-sectional view of another embodiment of the absorbent core according to the present invention.

Referring again to FIG. 2, in one embodiment, the absorbent core is constructed such that the second absorbent 26 is arranged near the baffle 14 and positioned vertically below the first absorbent 24. The absorbent core 16, however, may be constructed in any suitable manner such that at least part of the first absorbent 24 is vertically above the second absorbent 26, when in use. Alternatively, as shown in FIG. 7, the first absorbent 24 may be vertically below the second absorbent 26, when in use. The second absorbent 26 may be positioned vertically below the first absorbent 24 and above another absorbent layer similar or the same as the first absorbent 24. Advantageously, the first absorbent 24 and the second absorbent 26 can be arranged in any number of ways with adjacent layers of the same or different materials. The layers do not need to be the same size, shape, or coextensive with each other but may be if these arrangements are beneficial.

The second absorbent 26 includes absorbent fibers treated with a non-fugitive densification agent. As noted above, the phrase "non-fugitive densification agent" refers to any agent that has a volatility less than water, and/or that forms a hydrogen bond or other association with the fibers, or has an affinity for the fibers and provides an ability to decrease the force required to densify the fibrous mass or absorbent containing the fibers. As a result, the second absorbent will have a tensile strength in the dry state and virtually no tensile strength in the wet state.

The second absorbent 26 also includes a superabsorbent, which may be the same as or different from the superabsorbent used in the first absorbent 24, if a superabsorbent is present in the first absorbent 24. Desirably, if a superabsorbent is used in the first absorbent 24, then the superabsorbent used in the second absorbent 26 is the same as the superabsorbent used in the first absorbent 24.

The amount of superabsorbent used in the second absorbent 26 ranges from about 10% to about 70% by weight of the second absorbent 26, desirably from about 30% to about 60%, and more desirably from about 40% to about 55%. The amount of superabsorbent depends on the design absorbent capacity of the absorbent core of the absorbent article.

As noted above, the absorbent fibers used in the second absorbent 26 are treated with a non-fugitive densification agent. As a result, the second absorbent 26 may be densified using less force than would be needed if the densification agent was not present to achieve a density greater than about 0.15 g/cm$^3$, desirably between about 0.25 g/cm$^3$ to about 0.5 g/cm$^3$. The density of the second absorbent will be selected based on product thickness requirements and will also be dependent on superabsorbent content. For example, if the superabsorbent content is about 50%, a density of greater than about 0.3 g/cm$^3$ is usually desirable. Alternatively, if the superabsorbent content is lower, say about 30%, a density of 0.2 g/cm$^3$ may be acceptable. Furthermore, if only 15% superabsorbent is present, the desirable density of the second absorbent may be lower still, around 0.15 g/cm$^3$. A desirable absorbent fiber that has been treated with a densification agent is a special densification pulp that has a Kajanni equivalent of about 3.1 and a densification at 50 psi of about 0.16 g/cm$^3$. Such a pulp can be obtained from Weyerhauser Corporation under the trade designation ND-416.

Suitable non-fugitive densification agents are described in U.S. Pat. No. 6,425,979, the relevant portions of which are incorporated herein by reference. In general, therefore, the non-fugitive densification agent is selected from the group consisting of polymeric densification agents and non-polymeric densification agents that have at least one functional group that forms hydrogen bonds or coordinate covalent bonds with the fibers or exhibits an affinity for the fibers.

The polymeric densification agents may comprise polymeric densification agent molecules wherein the polymeric densification agent molecules have at least one hydrogen bonding functionality or coordinate covalent bond forming functionality. Preferred densification agents may further comprise repeating units, wherein the repeating units have such functionalities on each repeating unit of the polymer, although this is not necessary for adequate densification agent functions. In accordance with the present invention, the predetermined groups of polymeric densification agents include the group of densification agents consisting of polyglycols [especially poly(propyleneglycol)], a polycarboxylic acid, a polycarboxylate, a poly(lactone) polyol, such as diols, a polyamide, a polyamine, a polysulfonic acid, a polysulfonate, and combinations thereof. Specific examples of some of these compounds, without limitation, are as follows: polyglycols may include polypropylene glycol (PPG) and polyethylene glycol (PEG); poly(lactone) polyols include poly(caprolactone) diol and poly(caprolactone) triol; polycarboxylic acids include polyacrylic acid (PAA) and polymaleic anhydride; polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid; and copolymers thereof (for example a polypropylene glycol/polyethylene glycol copolymer). The polymeric densification agent typically has repeating units. The repeating unit may be the backbone of a compound, such as with a polypeptide, wherein the repeating polyamides occur in the peptide chain. The repeating unit may also refer to units other than backbones, for instance repeating acrylic acid units. In such a case, the repeating units may be the same or different. The densification agent has a functional group capable of forming a hydrogen bond or a coordinate covalent bond with the superabsorbent, and a functional group capable of forming a hydrogen bond with the fibers.

As used herein, a polymer is a macromolecule formed by chemical union of five or more identical or different combining units (monomers). A polyamine is a polymer that contains amine functional groups and a polyamide is a polymer that contains amide functional groups. Each of the densification agents has a hydrogen bonding or a coordinate covalent bonding functionality, and each of the densification agents may have such functionalities on each repeating unit (monomer) of the polymer. This repeating functionality may be a hydroxyl, a carboxyl, a carboxylate, a sulfonic acid, a sulfonate, an amide, an ether, an amine or combinations thereof. These densification agents are capable of forming hydrogen bonds because they have a functional group that contains an electronegative element, such as oxygen or a nitrogen.

The polyglycol has repeating ether units with hydroxyl groups at the terminal ends of the molecule. The polycarboxylic acid, such as polyacrylic acid, has a repeating carboxyl group in which a hydrogen is bound to an electronegative oxygen, creating a dipole that leaves the hydrogen partially positively charged. The polyamide (such as a polypeptide) or polyamine has a repeating NR group in which a hydrogen may be bound to an electronegative nitrogen that also leaves the hydrogen partially positively charged. The hydrogen in both cases can then interact with an electronegative atom, particularly oxygen or nitrogen, on the superabsorbent or fiber to form a hydrogen bond that adheres the densification agent to the superabsorbent and fiber. The electronegative oxygen or nitrogen of the densification agent also can form a hydrogen bond with hydrogen atoms in the superabsorbent or fiber that have positive dipoles induced by electronegative atoms, such as oxygens or nitrogens, to which the hydrogen is attached. The polyamide also has a carbonyl group with an electronegative oxygen that can interact with hydrogen atoms in the superabsorbents or fibers. Thus, the polymeric densification agents can enhance the hydrogen bonding (a) between the fibers and densification agent; and (b) in the case of superabsorbents with hydrogen bonding functionalities, between the densification agent and the superabsorbents.

Alternatively, the polymeric densification agent may form a coordinate covalent bond with the superabsorbents and a hydrogen bond to the fibers. The fibers themselves contain functional groups that can form hydrogen bonds with the densification agent, and allow the densification agent to adhere to the fiber. Cellulosic and synthetic fibers, for example, may contain hydroxyl, carboxyl, carbonyl, amine, amide, ether and ester groups that will hydrogen bond with the hydroxyl, carboxylic acid, carboxylate, amide or amine groups of the densification agent. Hence, the polymeric densification agent will adhere the superabsorbent with a coordinate covalent bond and the fiber will adhere with a hydrogen bond. Alternatively, the densification agent exhibits a high affinity for the fiber's surface such that it at least partially coats the fiber surface and remains present with minimal transfer to other surfaces in the dry state.

In some embodiments, the polymeric densification agent is bound to both the fibers and the superabsorbent by hydrogen bonds. A polypropylene glycol densification agent, for example, can be used to bind water-insoluble polyacrylate hydrogel superabsorbents to cellulosic fibers. The hydroxyl and ether groups on the glycol densification agent participate in hydrogen-bonding interactions with the hydroxyl groups on the cellulose fibers and the carboxyl groups on the polyacrylate hydrogel.

Alternatively, a polypropylene glycol (PPG) densification agent, for example, can be used to bind a water-soluble particle to cellulosic fibers. The hydroxyl and ether groups on the glycol densification agent participate in hydrogen bonding interactions with the hydroxyl groups on the cellulose fibers and appropriate functionalities on the water-soluble particle.

Therefore, the densification agent will adhere both the particle and fiber with hydrogen bonds. The presence of a hydrogen-bonding functionality on each repeating unit of the polymeric densification agent has been found to increase the number of hydrogen bonding interactions per-unit-mass of polymer, which provides superior binding efficiency and diminishes separation of materials from the fibers. The repeating ether functionality on the glycol densification agent provides this efficiency. A repeating carboxyl group is the repeating functionality on polyacrylic acid, while repeating carbonyls and NR groups (where R is H, alkyl, preferably lower alkyl i.e., less than five carbon atoms, in a normal or iso configuration) of the amide linkages are the repeating functionalities on polyamides such as polypeptides. A repeating amine group is present on polyamines.

The polymeric organic densification agents of the present invention are expected to increase in binding efficiency as the length of the polymer increases, at least within the ranges of molecular weights that are reported in the examples below. This increase in binding efficiency would be attributable to the increased number of hydrogen bonding or coordinate covalent bonding groups on the polymer with increasing molecular length. Each of the polymeric densification agents has a hydrogen bonding or coordinate covalent bonding functionality, and each such densification agent may have such functionalities on each repeating unit of the polymer. Accordingly, longer polymers provide more hydrogen bonding groups or coordinate covalent bonding groups that can participate in hydrogen-bonding interactions or in coordinate covalent bonds.

Although the invention is not limited to polymeric densification agents of particular molecular weights, polymeric densification agents having a molecular weight greater than 500 grams/mole are preferred because they provide attractive physical properties, and the solid is less volatile as compared to low-molecular-weight polymeric densification agents. Polymeric densification agents with molecular weights greater than about 4000 grams/mole are especially preferred because they have minimal volatility and are less likely to evaporate from the superabsorbents. Low-molecular weight materials typically are more mobile than are the higher-molecular weight materials. Low-molecular weight materials can more easily move to the fiber-superabsorbent interface, and are more easily absorbed by the fiber, thus making them less available to bond the superabsorbents to the fibers. The higher molecular weight materials are less apt to be absorbed by the fibers, and are less volatile than the low-molecular weight materials. As a result, higher molecular weight polymeric densification agents, to a greater extent, remain on the surface of the superabsorbents where they are more available to bond superabsorbents to fibers. In some embodiments, polymers with molecular weights between about 4000 and about 8000 grams/mole may be used. Polymers with molecular weights above about 8000 may be used, but such exceedingly high molecular weight polymers may decrease binding efficiency because of processing difficulties.

Certain polymeric densification agents have greater binding efficiency because their repeating functionality is a more efficient hydrogen bonding group. It has been found that repeating amide groups are more efficient than repeating carboxyl functionalities, which are more efficient than repeating hydroxyl functionalities, which in turn are more efficient than amine or ether functionalities. Therefore, polymeric densification agents may be preferred that have repeating amine or ether functionalities, desirably repeating hydroxyl functionalities, more desirably repeating carbonyl or carboxyl functionalities, and particularly desirable repeating amide functionalities. Binding may occur at any pH, but is suitably performed at a neutral pH of 5–8, preferably 6–8, to diminish acid hydrolysis of the resulting fibrous product. Suitable densification agents may be selected from the group consisting of polyglycols such as polyethylene glycol or polypropylene glycol, polycarboxylic acids such as polyacrylic acid, polyamides, polyamines, poly(lactone) polyols, such as poly(caprolactone) diol, and combinations or copolymers thereof.

The group consisting of polycarboxylic acids (such as acrylic acid), polyamides and polyamines has been found to have a especially good binding efficiency. Among polyamides, polypeptides are especially preferred.

As noted above, the non-fugitive densification agent may include non-polymeric densification agents. The non-polymeric densification agents have a volatility less than water. In general, they have a vapor pressure, for example, less than 10 mm Hg at 25° C., desirably less than 1 mm Hg at 25° C. The non-polymeric densification agents comprise molecules with at least one functional group that forms hydrogen bonds or coordinate covalent bonds with the fibers. In accordance with the present invention, the predetermined group of non-polymeric densification agents may include a functional group selected from the group consisting of a carboxyl a carboxylate, a carbonyl, a sulfonic acid, a sulfonate, a phosphate, a phosphoric acid, a hydroxyl, an amide, an amine, and combinations thereof (such as an amino acid or a hydroxy acid) wherein each densification agent includes at least two such functionalities, and the two functionalities are the same or different. A requirement for the non-polymeric densification agent is that it have a plurality of functional groups that are capable of hydrogen bonding, or at least one group that can hydrogen bond and at least one group that can form coordinate covalent bonds. As used herein, the term "non-polymeric" refers to a monomer, dimer, trimer, tetramer, and oligomers, although some particular non-polymeric densification agents are monomeric and dimeric, desirably monomeric.

Particularly suitable non-polymeric organic densification agents are capable of forming five or six membered rings with a functional group on the surface of the particle. An example of such a densification agent is an amine or amino acid (for example, a primary amine or an amino acid such as glycine) which forms six-membered rings by forming hydrogen bonds:

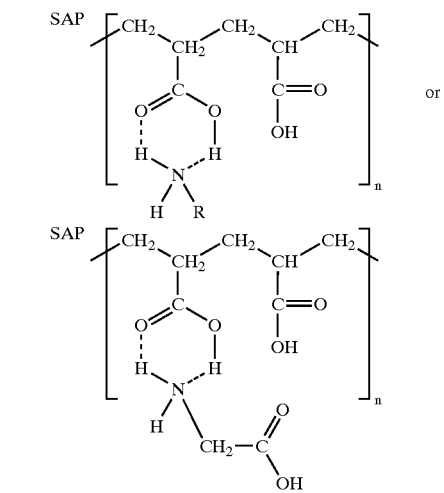

A six-membered ring also is formed by the hydroxyl groups of carboxylic acids, alcohols, and amino acids, for example:

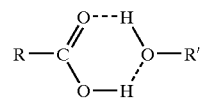

A five membered ring can be formed by the densification agent and the functionality on the surface of the particle, for example:

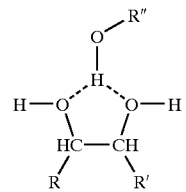

wherein the particle is a water-insoluble particle such as superabsorbent and the densification agent is an alcohol, such as a polyol with hydroxyl groups on adjacent carbons, for example 2,3-butanediol. A densification agent that forms a five-membered ring can also be used with a water-soluble particle, for example wherein the particle is EDTA and the densification agent is an alcohol, such as a polyol with hydroxyl groups on adjacent carbons, for example 2,3-butanediol.

Other alcohols that do not form a five-membered ring also can be used, for example alcohols that do not have hydroxyl groups on adjacent carbons. Examples of suitable alcohols include primary, secondary or tertiary alcohols.

Amino alcohol densification agents are alcohols that contain an amine group (—$NR_2$), and include densification agents such as ethanolamine (2-aminoethanol), and diglycolamine (2-(2-aminoethoxy)ethanol)). Non-polymeric polycarboxylic acids contain more than one carboxylic acid functional group, and include such densification agents as citric acid, propane tricarboxylic acid, maleic acid, butanetetracarboxylic acid, cyclopentanetetracarboxylic acid, benzene tetracarboxylic acid and tartaric acid. A polyol is an alcohol that contains a plurality of hydroxyl groups, and includes diols such as the glycols (dihydric alcohols) ethylene glycol, propylene glycol and trimethylene glycol; triols such as glycerin (1,2,3-propanetriol); esters of hydroxyl containing densification agents may also be used, with mono- and di-esters of glycerin, such as monoglycerides and diglycerides, being especially desired; and polyhydroxy or polycarboxylic acid compounds such as tartaric acid or ascorbic acid (vitamin C).

Hydroxy acid densification agents are acids that contain a hydroxyl group, and include hydroxyacetic acid ($CH_2OHCOOH$) and lactic, tartaric, ascorbic, citric, and salicylic acid. Amino acid densification agents include any amino acid, such as glycine, alanine, valine, serine, threonine, cysteine, glutamic acid, lysine, or β alanine.

Sulfonic acid densification agents and sulfonates are compounds that contain a sulfonic acid group ($—SO_3H$) or a sulfonate ($—SO_3^-$). Amino-sulfonic acids also can be used. One example of an amino-sulfonic acid densification agent suitable for the present invention is taurine, which is 2-aminoethanesulfonic acid.

Non-polymeric polyamide densification agents are small molecules (for example, monomers or dimers) that have more than one amide group, such as oxamide, urea and biuret. Similarly, a non-polymeric polyamine densification agent is a non-polymeric molecule that has more than one amine group, such as ethylene diamine, EDTA or the amino acids asparagine and glutamine.

Although other non-polymeric organic densification agents are suitable in accordance with the discussion above, the non-polymeric organic densification agent is desirably selected from the group consisting of glycerin, a glycerin monoester, a glycerin diester, glyoxal, ascorbic acid, urea, glycine, pentaerythritol, a monosaccharide, a disaccharide, citric acid, taurine, tartaric acid, dipropyleneglycol, an urea derivative, phosphate, phosphoric acid, and combinations thereof (such as hydroxy acids).

The non-polymeric densification agent also is more desirably selected from the group consisting of glycerin, a glycerin monoester, a glycerin diester, a polyglycerin oligomer, a propylene glycol oligomer, urea and combinations thereof (such as glycerin and urea). As used herein, an oligomer refers to a condensation product of polyols, wherein the condensation product contains less than ten monomer units. A polyglycerin oligomer as referred to herein means a condensation product of two or more glycerin molecules. A propylene glycol oligomer as referred to herein means a condensation product of two or more propylene glycol molecules. The non-polymeric densification agents also may include functionalities selected from the group consisting of a carboxyl, a carboxylate, a carbonyl, a sulfonic acid, a sulfonate, a phosphate, a phosphoric acid, a hydroxyl, an amine, an amide, and combinations thereof (such as amino acids and hydroxy acids). The non-polymeric densification agents may have at least two functionalities from such group, and the groups may be the same or different.

Each of the non-polymeric densification agents disclosed above is capable of forming hydrogen bonds because it has a functional group that contains electronegative atoms, particularly oxygens or nitrogens, or has electronegative groups, particularly groups containing oxygens or nitrogens, and that also may include a hydrogen. An amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an NR group in which a hydrogen may be bound to an electronegative nitrogen that also leaves the hydrogen partially positively charged. The partially positively charged hydrogen in both cases then can interact with an electronegative element, such as oxygen or nitrogen, on the particle or fiber to help adhere the densification agent to the particle and fiber. The polycarboxylic acid, hydroxy acid, amino acid and amide also have a carboxyl group with an electronegative oxygen that can interact with hydrogen atoms in the particles and fibers, or in intermediate molecules between the densification agent and particles or fibers. Similarly, electronegative atoms (such as oxygen or nitrogen) on the fiber or particle can interact with hydrogen atoms on the densification agent that have positive dipoles, and partially positive hydrogen atoms on the fiber or particle can interact with electronegative atoms on the densification agent.

Several proposed hydrogen bonding interactions of two of the densification agents (glycine and 1,3-propanediol) with cellulose are shown in U.S. Pat. No. 6,425,979, the relevant portion of which is incorporated herein by reference. The hydrogen bonding interactions are shown as dotted lines. One such interaction is shown between the nitrogen of glycine and a hydrogen of an —OH on cellulose. A hydrogen bond with glycine is also shown between an oxygen of the —OH on glycine and the hydroxy hydrogen of an alcohol side chain on cellulose. Hydrogen bonding interactions of the 1,3-propanediol are shown in dotted lines between an oxygen on an —OH group of the densification agent and a hydrogen of an —OH group on the cellulose molecule. Another hydrogen bond is also shown between a hydrogen on an —OH group of the glycol densification agent and an oxygen in an alcohol side chain of the cellulose.

It also is possible for water or other hydrogen bonding molecules to be interposed between the fiber and densification agent, such that the fiber and densification agent are both hydrogen bonded to the water molecule.

In some embodiments, the densification agent is bound to both the fibers and the particle by hydrogen bonds. A polyol densification agent, such as a diol, for example, can be used to bind polyacrylate hydrogel particles to cellulosic fibers. The hydroxyl groups on the polyol densification agent participate in hydrogen-bonding interactions with the hydroxyl groups on the cellulose fibers and the carboxyl groups on the polyacrylate hydrogel. As a result, the densification agent will adhere to both the particle and fiber with hydrogen bonds. These hydrogen bonds provide excellent binding efficiency and diminish separation of bound particles from the fibers.

Particularly efficient hydrogen bonding densification agents include those with carboxyl groups, such as ascorbic acid, or amide groups, such as urea. Hydroxyl groups are also very efficient densification agents. Amine and ether functionalities are less efficient densification agents.

Densification agents have functional groups that may be selected independently or in combination from the group consisting of a carboxyl, a carboxylate, a carbonyl, a hydroxyl, a sulfonic acid, a sulfonate, a phosphoric acid, a phosphate, an amide, an amine, and combinations thereof. These functional groups might be provided by the following exemplary chemical compounds: a carboxyl group could be provided by carboxylic acids, such as ascorbic acid; a carboxylate, which is an ionized carboxylic acid, could be provided by a material such as potassium citrate; a carbonyl group can be provided by an aldehyde or ketone; a hydroxyl can be provided by an alcohol or polyol, such as glycerol, or a mono- or diglyceride, which are esters of glycerol; an amide, such as a urea; and an amine, which may be provided by an alkyl amine, such as ethanolamine, wherein the densification agent has at least two of these functional groups, and each of the functional groups can be the same (for example, a polyol, polyaldehyde, polycarboxylic acid, polyamine or polyamide) or different (for example, an amino alcohol, hydroxy acid, hydroxyamide, carboxyamide, or amino acid). Functional groups also may be selected independently or in combination from the group consisting of carboxyl, an alcohol, an amide and an amine. An aldehyde may optionally be a member of each of these groups, particularly if it is oxidized to a carboxylic acid.

The second absorbent 26 can be produced on a conventional online absorbent drum former by homogeneously mixing high levels of superabsorbent and fluff pulp in a forming chamber as described in U.S. Pat. Appln. Pub. US 2002/0156441 A1 to Sawyer et. al., the relevant portions of which are incorporated herein by reference. Superabsorbent loss can be minimized by the use of a woven polyester fabric, suitably with about 300 micron pores, wrapped about the forming drum to cover the forming screens. Alternatively, micro-perforated forming screens with openings of approximately 300 microns or smaller may also be used. The openings in the fabric or screens should be small enough to trap most of the superabsorbent particles while leaving enough open area to maintain high enough permeability for pad formation.

By using an online drum former, as opposed to an offline former, extra mass and capacity of the absorbent material can be placed in zones where the material is most useful. For example, the second absorbent 26 can be formed to a specific shape, such as hourglass or the like, or extra mass can be positioned in a specific area by creating a deeper pocket in the forming screen. The second absorbent 26 may be placed on a carrier or wrap tissue or similar material. When the second absorbent 26 is formed, it leaves the forming chamber at a low density and can then be densified.

Figure 4:
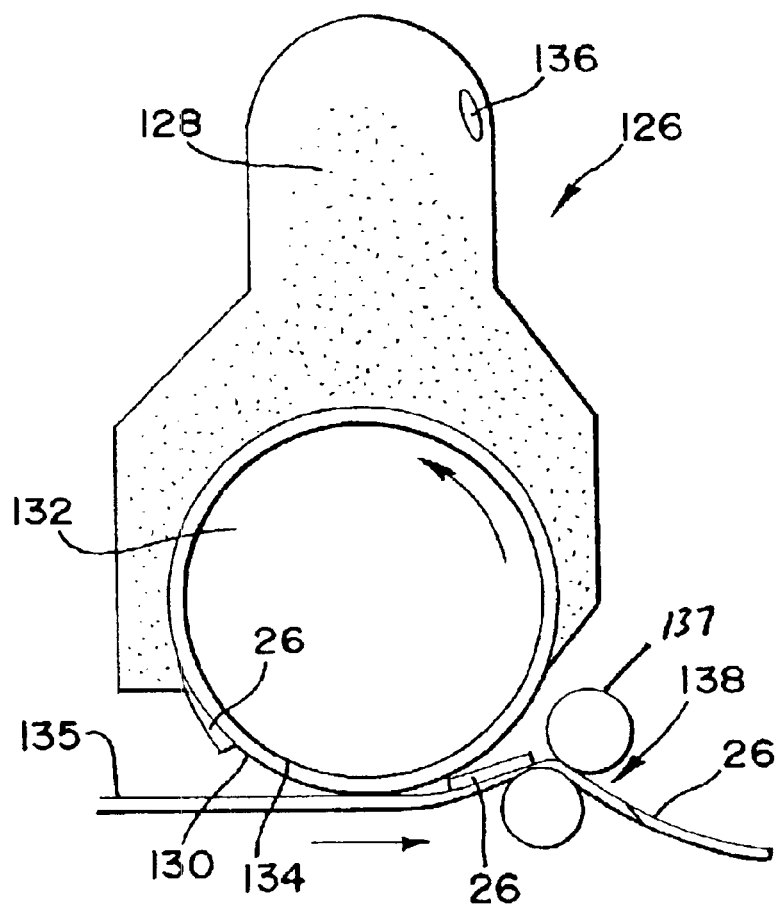
FIG. 4 is a plan view of an apparatus used to make the second absorbent shown in FIG. 2.

As shown in FIG. 4, the superabsorbent and the fluff pulp can be homogeneously mixed in a forming chamber 128 of the drum former 126. Man-made fibers or carrier particles can also be mixed with the superabsorbent and the fluff pulp. To minimize superabsorbent loss during forming, a porous fabric 130, such as a woven polyester fabric with approximately 300 micron pores, can be wrapped around a forming drum 132 of the drum former 126 to cover a forming screen 134 on the forming drum 132. Alternatively, fine pore, or micro-perforated, forming screens can be used in place of conventional forming screens 134. As another alternative, a light layer of fluff pulp-rich composite can be directed to the forming screens 134 prior to having the high-superabsorbent composition reach the forming screens 134 within the forming chamber 128. In any case the effective openings of the screen surface are less than 300 microns. The permeability of the forming surface must be high enough to form a uniform pad and the forming surface must be durable. This combination of properties dictates a pore size between 75 and 300 microns. The forming screens 134, whether conventional or fine pore, can be either flat screens or shaped pad zoned absorbent screens. Such a process is further described in U.S. Pat. Appln. Pub. US 2002/0156441 A1 to Sawyer et. al., the relevant portions of which are incorporated herein by reference.

By using an online drum former 126, as opposed to producing the second absorbent 26 offline, additional mass of the homogeneously mixed superabsorbent material and pulp fluff can be directed into at least one area of the second absorbent 26 where extra absorbent material would be most useful. In addition, it is easy to vary the overall absorbent capacity of the absorbent core 16 and thus the article 10 by varying the amount of superabsorbent and/or pulp fluff as desired by manufacturing and consumer requirements. As a result, capacities from 20 grams up to 1200 grams or more can easily be affected by simply using a drum former 126 as described above and by varying the amount of fluff and/or superabsorbent.

A nozzle 136 can be placed in a top front position on the forming chamber 128 to disperse the superabsorbent and to enable homogeneous mixing of the superabsorbent and the fluff pulp. Examples of such are described in U.S. Pat. Nos. 6,207,099 and 6,267,575, the relevant portions of which are incorporated herein by reference. Alternatively the nozzle 136 can be positioned to provide a gradient of composition within the second absorbent 26.

The second absorbent 26 leaves the forming chamber 128 at a low density, namely less than 0.1 g/cm$^3$, and must be densified. The second absorbent 26 may be deposited on a conveyor or carrier tissue 135. The second absorbent 26 is then compacted to a density of at least 0.25 g/cm$^3$ and suitably at least 0.30 g/cm$^3$. The densification can be accomplished with a conventional compaction roll 137, or more suitably, with a heated nip 138 as shown in FIG. 4. The heated nip 138 is suitably heated to about 80° to about 150° C.

The second absorbent 26 can be produced with a basis weight of between about 80 and 1000 gsm, suitably between about 100 and 800 gsm, more suitably between about 120 and 750 gsm. Once the second absorbent 26 is densified, the second absorbent can have any suitable thickness such that the overall thickness $t_1$ of the absorbent article 10 is less than about 10 millimeters. Put another way, the second absorbent 26 has a thickness such that the thickness $t_2$ of the absorbent core 16 ranges from about 2 mm to about 8 mm. In general, therefore, the second absorbent 26 has a thickness of between about 0.2 and 5 mm, suitably between about 0.5 and about 3 mm, more suitably between about 0.6 and about 2 mm.

During the forming process, the mixture of superabsorbent and pulp fluff can be humidified to improve densification of the resulting second absorbent 26 and provide lower cylindrical compression or stiffness values. The use of heat and humidity in the absorbent composite densification process is taught, for example, in U.S. Pat. No. 6,214,274, which is incorporated herein by reference. Furthermore, a pattern can be embossed onto the second absorbent 26 to reduce stiffness.

Figure 6:
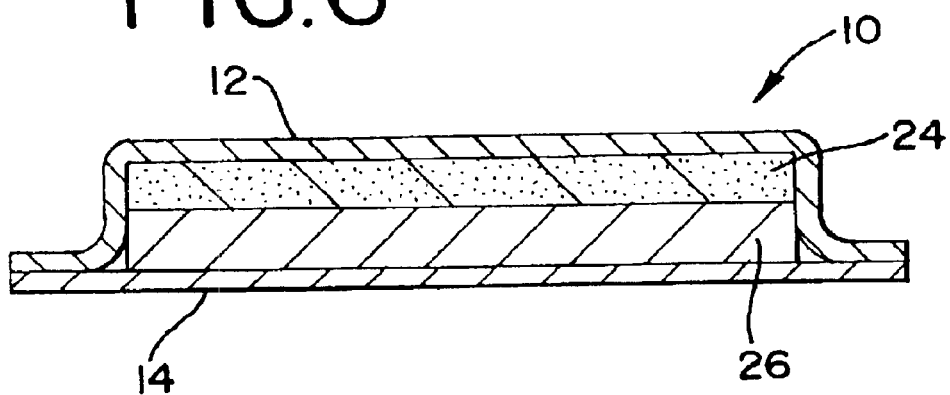
FIG. 6 is a cross-sectional view of one embodiment of the absorbent core according to the present invention.
Figure 8:
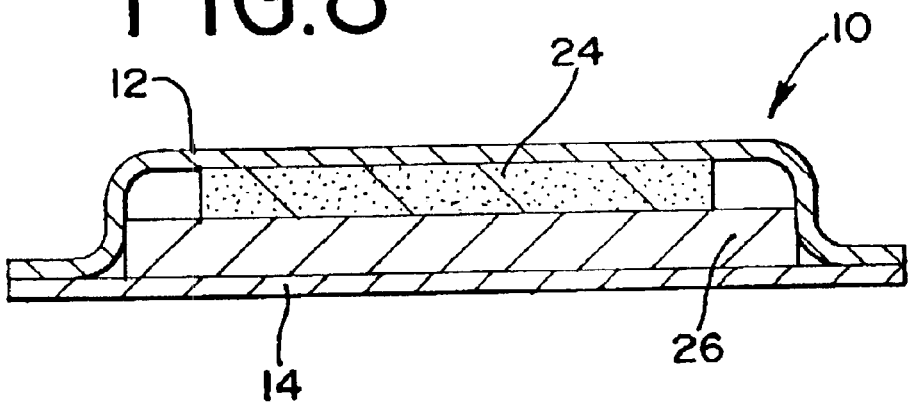
FIG. 8 is a cross-sectional view of another embodiment of the absorbent core according to the present invention.

Referring back to FIG. 1, the first absorbent 24 and the second absorbent 26 can have any suitable length. For example, the second absorbent 26 may have a length that is less than, equal to, or greater than the length of the first absorbent 24. Likewise, the first absorbent 24 and the second absorbent 26 may have any suitable width. For example, as shown in FIGS. 2 and 7, the first absorbent 24 has a width greater than the width of the second absorbent 26. As shown in FIG. 6, the width of the first absorbent 24 and the second absorbent 26 are substantially the same. As shown in FIG. 8, the width of the first absorbent 24 is less than the width of the second absorbent 26.

Referring to FIG. 2, the absorbent article 10 is shown having a thickness $t_1$ of less than about 10 mm. Desirably, the absorbent article 10 has a thickness $t_1$ of from between about 7 mm to about 8 mm. More desirably, the absorbent article 10 has a thickness $t_1$ of about 5 mm. The thickness $t_1$, or caliper of the absorbent article 10 can be determined by measuring the thickness $t_1$ of the absorbent article 10 with a bulk tester such as a Digimatic Indicator Gauge, type DF 1050E which is commercially available from Mitutoyo Corporation of Japan. Typical bulk testers utilize a smooth platen that is connected to the indicator gauge. The platen has dimensions that are smaller than the length and width of the second absorbent 26. The thickness of the absorbent article 10 is generally measured under a pressure of 1.4 kPa at about room temperature (23° C.) and at about 50% relative humidity. The density in grams per cubic centimeter of absorbent materials is determined by dividing the basis weight in grams per square meter by the product of the thickness in centimeters and 10,000 (density (g/cc)=basis weight (gsm)/(thickness (cm)*10,000).

Still referring to FIG. 2, the absorbent core 16 also has a thickness $t_2$ of less than about 5 mm. Desirably, the absorbent core 16 has a thickness $t_2$ ranging from between about 2 mm to about 4 mm. More desirably, the absorbent core 16 has a thickness $t_2$ of less than about 3 mm. The thickness $t_2$ of the absorbent core 16 can be measured in a similar fashion as the thickness t₁ of the absorbent article 10 except that the absorbent core 16 will first be removed from the absorbent article 10.

The absorbent article 10 further is shown having a garment adhesive 40 secured to an exterior surface of the baffle 14. The garment adhesive 40 can be a hot or cold melt adhesive that functions to attach the absorbent article 10 to the inner crotch portion of an undergarment during use. The garment adhesive 40 enables the absorbent article 10 to be properly aligned and retained relative to the user's urethra so that maximum protection from the involuntary loss of urine can be obtained. The garment adhesive 40 can be slot coated onto the baffle 14 as one or more strips or it can be applied as a swirl pattern. The composition of the garment adhesive 40 is such that it will allow a user to remove the absorbent article 10 and reposition the article 10 in the undergarment if needed. A suitable garment adhesive 40 that can be used is Code Number 34-5602 which is commercially available from National Starch and Chemical Company. National Starch and Chemical Company has an office located at 10 Finderne Avenue, Bridgewater, N.J.

In order to protect the garment adhesive 40 from contamination prior to use, a releasable peel strip 42 is utilized. The peel strip 42 can be formed from paper or treated paper. A standard type of peel strip 42 is a white Kraft peel paper coated on one side so that it can be easily released from the garment adhesive 40. The user removes the peel strip 42 just prior to attaching the absorbent article 10 to the inner crotch portion of his or her undergarment. Three suppliers of the peel strips 42 include Tekkote, International Paper Release Products, and Namkyung Chemical Ind. Co., Ltd. Tekkote has an office located at 580 Willow Tree Road, Leonia, N.J. 07605. International Paper Release Products has an office located at 206 Garfield Avenue, Menasha, Wis. 54952. Namkyung Chemical Ind. Co., Ltd. has an office located at 202-68 Songsan-ri, Taean-eup, Hwaseoung-kum, Kyunggi, Korea. Absorbent articles that are not attached to the user's underwear such as disposable diapers and adult incontinence garments (briefs, undergarments, protective underwear) do not require garment adhesive.

Figure 5:
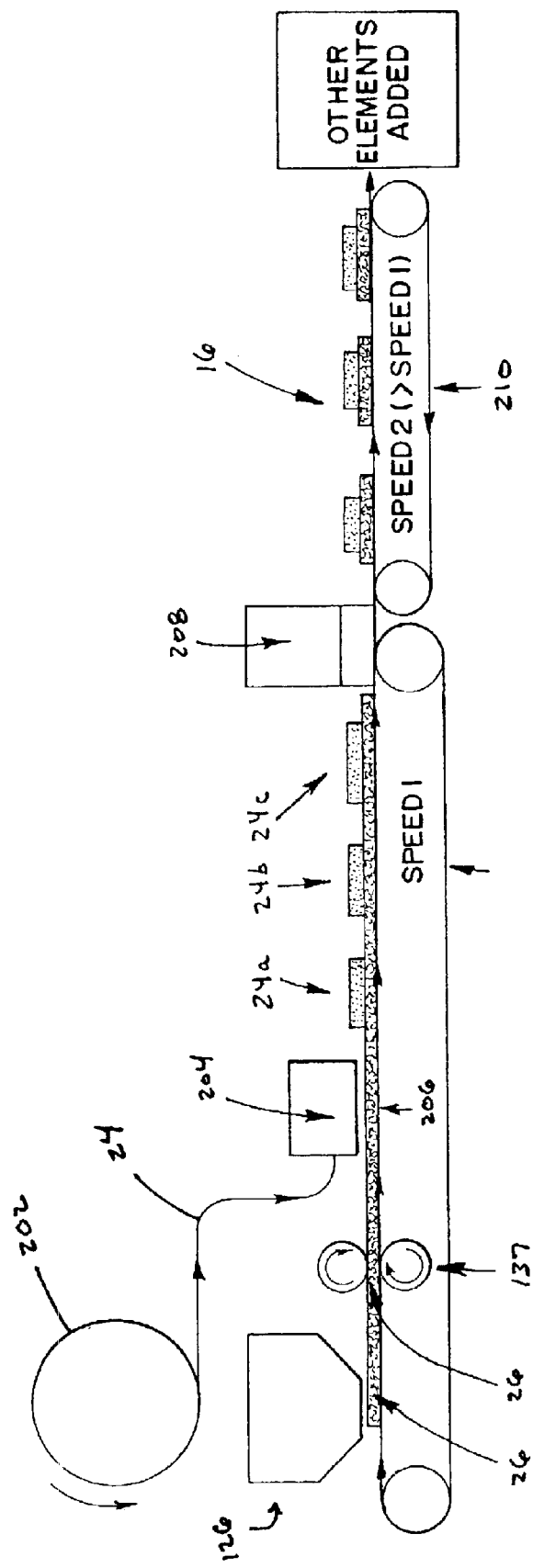
FIG. 5 is a schematic of a process for making the absorbent core according to the present invention.

Turning now to FIG. 5 a schematic of a process for making the absorbent core 16 of the present invention is shown. The process includes providing the material forming the first absorbent layer 24, which may be provided as a preformed layer by a roll 202. The material forming second absorbent layer 26 is provided as described above with respect to FIG. 4. The material forming the first absorbent layer 24 is fed to a cutting unit 204 where it is cut into individual pads or sections 24a, 24b, 24c and placed onto the material forming the second absorbent layer 26, which is fed under the cutting unit 204 by a first conveyer 206. Thereafter, the material forming the second absorbent layer 26 is cut at the timed cutting unit 208 so that the first absorbent layer 24 and the second absorbent layer 26 leave the timed cutting unit 208 together as the core 16. Each unit of a first absorbent layer 24 and second absorbent layer 26 are separated from each other by providing a second conveyor 210 having a speed greater than the speed of the first conveyer. Thereafter, the core 16, which includes the first absorbent layer 24 and the second absorbent layer 26, may be conveyed to one or more finishing stations 212 depending on the final configuration of the article 10. For example, the core 16 may be conveyed to a station that provides a baffle and/or bodyside liner.

It has been found that the process according to the present invention can provide an absorbent layer having a desired density without detrimentally affecting the superabsorbent.

EXAMPLES

The following examples are presented to more fully describe the present invention and should not be interpreted as limiting the invention in any way.

Liquid Saturated Retention Capacity

The following test was conducted to determine the amount of fluid retained by the absorbent core 16 and/or absorbent article 10. The liquid saturated retention capacity is determined as follows. The material to be tested, having a moisture content of less than about 7 weight percent, is weighed and submerged in an excess quantity of a 0.9 weight percent aqueous saline solution at room temperature (about 23° C.). The material to be tested is allowed to remain submerged for 20 minutes. After the 20 minute submerging, the material is removed and, referring to FIG. 9, placed on a TEFLON™ coated fiberglass screen 104 having 0.25 inch (0.6 cm) openings (commercially available from Taconic Plastics Inc., Petersburg, N.Y.) which, in turn, is placed on a vacuum box 100 and covered with a flexible rubber dam material 102. A vacuum of about 0.5 pound per square inch (about 3.5 kilopascals) is drawn on the vacuum box for a period of about 5 minutes with the use of, for example, a vacuum gauge 106 and a vacuum pump 108). The material being tested is then removed from the screen and weighed.

The amount of liquid retained by the material being tested is determined by subtracting the dry weight of the material from the wet weight of the material (after application of the vacuum), and is reported as the absolute liquid saturated retention capacity in grams of liquid retained. If desired, the weight of liquid retained may be converted to liquid volume by using the density of the test liquid, and is reported as the liquid saturated retention capacity in milliliters of liquid retained. The lower the number, the less fluid the product can retain under pressure.

For relative comparisons, this absolute liquid saturated retention capacity value can be divided by the weight of the tested material to give the specific liquid saturated retention capacity in grams of liquid retained per gram of tested material. If material, such as hydrogel-forming polymeric material or fiber, is drawn through the fiberglass screen while on the vacuum box, a screen having smaller openings should be used. Alternatively, a piece of tea bag or similar material can be placed between the material and the screen and the final value adjusted for the liquid retained by the tea bag or similar material.

Cylindrical Compression Value

The cylindrical compression test is used to measure the force value (peak load), load value at 50% strain, and peak energy that relates to the stiffness of a 50×300 mm cylindrically-shaped piece of material. The peak load value can be expressed as an absolute force in grams or as grams/gsm which is derived by dividing the peak load value by the basis weight of the absorbent material expressed in grams per square meter (gsm). The compression of the cylindrically shaped absorbent material gives a maximum force value of stiffness in the edgewise direction. The higher the value, the stiffer the specimen. When the stiffness value is not too high, the absorbent material will not be perceived as "stiff" by the wearer of the absorbent article. Typically, a lower value may be perceived as more desirable than a higher value, although the ideal value can be consumer dependent. For infant diapers, for example, a value below about 6 grams/gsm is desired. When the stiffness value is too high, the absorbent material may cause discomfort to the user that could result in a negative perception of comfort by the wearer.

A 50 mm×300 mm (2" by 12") rectangular shape specimen is obtained and formed into the shape of a cylinder by aligning the ends of the specimen and stapling the ends together. A load cell such as one obtained from MTS Systems Corp. Research Triangle Park, N.C. having compression plates and a load range of from about 0 to about 5000 grams is used as a force measurement gauge. The initial plate separation (gage length) is about 56 mm. The sample is placed on the bottom compression plate and the top compression plate is lowered on the specimen for about a 30.5 mm gage length at a speed of 25 mm/min and the force is measured and recorded. The maximum force (peak load) in grams and the load at 50% specimen strain can also be measured and recorded. For relative comparisons, the peak load or the load at 50% specimen strain can be divided by the basis weight of the specimen to give load per basis weight of specimen. This test method is further described in U.S. Pat. No. 6,323,388, the relevant portion of which is incorporated herein by reference.

Example 1

Absorbent layers were prepared and are shown in Table 1. Samples 1A–1C contained 50% by weight of a Kraft pulp with 16% hardwood content supplied by Bowater Fibers, Childersburg, Ala. and 50% by weight of a superabsorbent known as Dow DRYTECH 2035 obtained from Dow, Midland, Mich. Samples 2A–2C contained 50% by weight of a fiber treated with a non-fugitive densification agent and is commercially available as ND-416 by Weyerhauser Co. and 50% by weight of a superabsorbent known as Dow DRYTECH 2035. Each of the samples had a basis weight of 472 gsm. The samples were made by mixing equal proportions of fiber and superabsorbent as specified above in a forming chamber. A 472 gsm uncompressed mat of fiber and superabsorbent for each code was deposited on a forming wire. The resulting mat of fibers and superabsorbent was passed under a compression nip formed from two steel rolls with a gap. The gap was adjusted to achieve a web with the desired bulk and hence density. For the ND-416 pulp with the densifying agent, the gap was wider than for the CR-1654 material indicating that less force was needed to densify the ND-416 material. The gaps required to form each density for each pulp/superabsorbent combination are presented in Table 1.

The compression roll gap, retention capacity, and cylindrical compression of each of the samples were tested according to the methods described above and the results are shown in Table 1.

TABLE 1

| Sample/Density (g/cm$^3$) | Compression Roll Gap (mm) | Retention Capacity (g/g) | Cylindrical Compression (g) | (g/gsm) |
|---|---|---|---|---|
| 1A, 0.15 | 0.47 | 18.4 | 438 | 0.93 |
| 1B, 0.26 | 0.25 | 17.8 | 917 | 1.94 |
| 1C, 0.35 | 0.01 | 17.4 | 1483 | 3.14 |
| 2A, 0.15 | 0.56 | 19.2 | 309 | 0.66 |
| 2B, 0.26 | 0.41 | 18.8 | 590 | 1.25 |
| 2C, 0.35 | 0.25 | 18.6 | 1061 | 2.24 | g = grams

It can be seen that samples 2A–2C have a greater retention capacity at a higher density than do the comparable samples 1A–1C. In addition, samples 2A–2C exhibit a lower cylindrical compression stiffness than the comparable samples 1A–1C. It is apparent that larger gaps and therefore less pressure is required to achieve a given density with the ND-416 pulp for samples 2A to 2C meaning it is easier to manufacture a thin absorbent using a pulp treated with a non-fugitive densification agent. As a result, it is expected that an absorbent layer that is made using a fibers treated with a non-fugitive densification agent will exhibit increased retention capacity and increased perception of softness as compared to an absorbent layer that does not contain fibers treated with a densification agent.

Example 2

Prototype pantyliners were made that included an absorbent core that will be described in more detail below. The pantyliners also included a polyethylene film backsheet plus a 22 gsm Sawabond 4346 bonded carded web bodyside liner produced by Sandler Vliesstoffwerk GmbH. & Co. KG located at Schwarzenbach An Der Saale, Germany. Between the liner and the absorbent layers there was also a 40 gsm bonded carded web layer produced by Shalag Shamir Nonwoven Fabric Industry located in Upper Galilee, Israel. The specifics of each sample are set forth in Table 2.

The absorbent core contained a first absorbent layer vertically above a second absorbent layer. The first absorbent layer was a bonded airlaid material. The upper absorbent layer was formed using 31% by weight Stockhausen FAVOR SXM-880 superabsorbent, 9% by weight Trevira 2 denier 3 mm Type 255 bicomponent binder fiber, and 60% Weyerhaueser NB-416 Kraft pulp and it had a dry tensile strength of about 23 to 26 N/50 mm. The second absorbent layer contained fibers treated with a densification agent commercially available as ND-416 from Weyerhaeuser as well as a superabsorbent, which was obtained as Dow DRYTECH 2035M from Dow. The specifics of each sample are set forth in Table 2.

The pantyliners were tested to determine their retention capacity and thickness and the results are set forth in Table 2.

TABLE 2

Pantyliner Prototypes

| Sample | Upper over Lower | SA (%) | Fiber (%) | Density (g/cc) | Thickness (mm) | Ret. Cap. (g) |
|---|---|---|---|---|---|---|
| A control | 200 gsm bonded airlaid | 31 | 69 | 0.193 | 1.04 | N/A |
|  | 2 × 200 gsm bonded airlaid | 31 | 69 | 0.193 | 2.08 | N/A |
|  | Total: | N/A | N/A | N/A | 3.12 | 54 |
| B | 180 gsm bonded airlaid | 31 | 69 | 0.2 | 0.9 | N/A |
|  | 300 gsm fluff (ND-416)/SA | 50 | 50 | 0.35 | 0.86 | N/A |
|  | Total | N/A | N/A | N/A | 1.76 | 52 |
| C | 180 gsm bonded airlaid | 31 | 69 | 0.2 | 0.9 | N/A |
|  | 300 gsm fluff (ND-416)/SA | 50 | 50 | 0.18 | 1.7 | N/A |
|  | Total | N/A | N/A | N/A | 2.6 | 52 |
| D | 180 gsm bonded airlaid | 31 | 69 | 0.2 | 0.9 | N/A |
|  | 300 gsm fluff (ND-416)/SA | 35 | 65 | 0.35 | 0.86 | N/A |
|  | Total | N/A | N/A | N/A | 1.76 | 46 |
| E | 180 gsm bonded airlaid | 31 | 69 | 0.2 | 0.9 | N/A |
|  | 300 gsm fluff (ND-416)/SA | 35 | 65 | 0.18 | 1.7 | N/A |
|  | Total | N/A | N/A | N/A | 2.6 | 47 |

SA = superabsorbent

It is seen that those samples with a greater superabsorbent content had a higher retention capacity. As noted above, the capacity of the absorbent core can be controlled by modifying the basis weight and/or the superabsorbent content in the second layer. It is also seen that samples B and D, which have a second absorbent layer that contains fibers treated with a densification agent and have a higher density, are thinner but have a capacity substantially the same as sample A.

Example 3

Prototype adult absorbency pads were made with an absorbent core having a first absorbent layer vertically above a second absorbent layer. The first absorbent layer was made by Concert Industries, Thurso Quebec Canada and it contained 30% by weight Stockhausen FAVOR SXM-880 superabsorbent, 5% KoSa 2 denier 6 mm type T255 bicomponent binder fiber, 65% Weyerhaeuser NB-416 pulp and it had a tensile strength of about 45 N/50 mm. The second absorbent layer contained a superabsorbent which was obtained as Dow DRYTECH 2035M from Dow and contained fibers treated with a densification agent commercially available as ND-416 from Weyerhaeuser. The specifics of each sample are set forth in Table 3.

The pads also included a polyethylene backsheet as a moisture barrier. On the bodyside there was a wettable 17 gsm rib knit spunbonded liner material. Between the liner and the absorbent there was a wettable 50 gsm meltspun surge material. Both materials are available from Kimberly-Clark Corporation, Dallas, Tex.

strength was measured using a tester such as a Model 4201 Instron with Microcon II from Instron Corp. Canton, Mass. The machine is calibrated by placing a 100 gram weight in the center of the upper jaw, perpendicular to the jaw and hanging unobstructed. The tension cell used is a 5 kilogram electrically-calibrating self-identifying load cell. The weight is then displayed on the Microcon display window. The procedure is performed in a room with standard-condition atmosphere such as about a temperature of about 23° C. and a relative humidity of about 50 percent.

A rectangular sample 5 cm by about 12 cm is cut from a piece of the absorbent material. The dry sample is then placed in the pneumatic action grips (jaws) with 1 inch (2.54 cm) by 3 inch (7.62 cm) rubber coated grip faces. The gauge

TABLE 3

Extra Plus Pad Prototypes

| Sample | Upper over Lower | SA (%) | Fiber (%) | Density (g/cc) | Thickness (mm) | Ret. Cap. (g) |
|---|---|---|---|---|---|---|
| F Control | 910 gsm fluff/SA | 43.5 | 56.5 | 0.13 | 7.0 | N/A |
| | 425 gsm fluff/SA | 11.8 | 88.2 | 0.18 | 2.36 | N/A |
| | Total | N/A | N/A | N/A | 9.36 | 256 |
| G | 400 gsm bonded airlaid | 30 | 70 | 0.15 | 2.67 | N/A |
| | 472 gsm fluff (ND-416), SA | 50 | 50 | 0.35 | 1.35 | N/A |
| | Total | N/A | N/A | N/A | 4.02 | 239 |
| H | 400 gsm bonded airlaid | 30 | 70 | 0.15 | 2.67 | N/A |
| | 472 gsm fluff (ND-416), SA | 50 | 50 | 0.18 | 2.62 | N/A |
| | Total | N/A | N/A | N/A | 5.29 | 243 |
| I | 400 gsm bonded airlaid | 30 | 70 | 0.15 | 2.67 | N/A |
| | 472 gsm fluff (ND-416), SA | 30 | 70 | 0.18 | 2.60 | N/A |
| | Total | N/A | N/A | N/A | 5.29 | 221 |
| J | 400 gsm bonded airlaid | 30 | 70 | 0.15 | 2.67 | N/A |
| | 472 gsm fluff (ND-416), SA | 30 | 70 | 0.35 | 1.35 | N/A |
| | Total | N/A | N/A | N/A | 4.02 | 221 |

SA = superabsorbent

It is seen that those samples with a greater density lower layer (second absorbent in this case) as compared to those with a lower density do not exhibit a sacrifice in capacity (compare, for example, samples G and H). They are, however, substantially thinner. In addition, a reduction in the amount of superabsorbent reduced the retention capacity (compare, for example, samples H and I) illustrating that modification of the composition of the second absorbent can be used to control the capacity of the final product.

Example 4

Absorbents according to the present invention were prepared and their tensile strength was measured. The tensile length is 10 cm) and the crosshead speed is 25 cm/minute. The crosshead speed is the rate at which the upper jaw moves upward pulling the sample until failure. The Tensile Strength value is the maximum load at failure, recorded in grams of force needed to permanently stretch or tear the sample. The tensile strength is evaluated for the material in both a dry condition and a 100 percent liquid saturated condition. The tensile strength for the material in a 100 percent liquid saturated condition is done by placing a dry sample in a container containing a sufficient excess of 0.9% saline solution for 20 minutes, after which the sample is placed in the jaws and the tensile strength is measured as described above. Table 4 shows the results.

TABLE 4

| Code | Upper over Lower | SA % | Fiber % | Density g/cc | Thickness mm | Dry Tensile, grams | Wet Tensile grams |
|---|---|---|---|---|---|---|---|
| 1 | 200 gsm bonded airlaid | 31 | 69 | 0.193 | 1.04 | 3127 | 817 |

TABLE 4-continued

| Code | Upper over Lower | SA % | Fiber % | Density g/cc | Thickness mm | Dry Tensile, grams | Wet Tensile grams |
|---|---|---|---|---|---|---|---|
| 2 | 472 gsm fluff (CR1654)/SAP | 50 | 50 | 0.15 | 3.14 | 99 | 0 |
| 3 | 472 gsm fluff (CR1654)/SAP | 50 | 50 | 0.35 | 1.35 | 202 | 0 |
| 4 | 472 gsm fluff (ND-416)/SAP | 50 | 50 | 0.15 | 3.14 | 86 | 0 |
| 5 | 472 gsm fluff (ND-416)/SAP | 50 | 50 | 0.35 | 1.35 | 585 | 0 |
| 6 | 100 gsm bonded airlaid | 0% | 100% | 0.067 | 1.50 | 2795 | 1389 |

SA = Superabsorbent
Note 1:
Composition of 100 gsm bonded airlaid material was 83% NB-416 pulp and 17% binder fiber (KoSa 2 denier 6 mm type T255 bicomponent binder fiber).
Note 2:
Composition of 200 gsm bonded airlaid material was 31% by weight Stockhausen SXM-880 superabsorbent, 9% bicomponent binder fiber (KoSa 2 denier 6 mm type T255 bicomponent binder fiber), 60% Kraft pulp
Note 3:
ND-416 is a densification pulp supplied by Weyerhaueser Co.
CR-1654 is a Kraft pulp with 16% hardwood content supplied by U.S. Alliance, Childersburg, Alabama.
SA for all lower layers was Dow DRYTECH 2035.

As seen from Table 4, the bonded airlaid materials maintain a significant tensile strength, even when wet (compare codes 1 and 6 with codes 2–5). In fact, the unbonded material (codes 2–5) do not have any tensile strength when wet. In addition, the unbonded materials that have a higher density have a greater dry tensile strength than those unbonded materials that have a lower density (compare codes 3 and 5 with codes 2 and 4).

Example 5

Several prototype thin pads with a design retention capacity of about 100 grams were tested in a confidential small scale study with consumers of POISE® Thin pads available from Kimberly-Clark. The POISE® thin pad was the control product.

Twenty four incontinent panelists were recruited to participate in this study. The study was six cells, four panelists per cell. Thirteen compared the prototypes R, L, and N to the control C. The other 11 compared the prototypes to each other. The panelists wore and used each code for four days and then participated in focus groups. In other words, the cells were arranged as follows: Cell 1: C vs. R; Cell 2: C vs. L; Cell 3: C vs. N; Cell 4: R vs. L; Cell 5: L vs. N; Cell 6: R vs. N.

The code definitions are listed below:

| Code | Description |
|---|---|
| C | POISE ® Thin |
| R | First absorbent layer with a basis weight of 200 gsm and containing 31% by weight superabsorbent (Stockhausen SXM-880), 9% bicomponent binder fiber, 60% Kraft pulp in a rectangular shape with a tensile strength of about 25 to 27 N/50 mm and vertically above the second absorbent layer with a basis weight of 290 gsm and containing 50% ND-416 and 50% superabsorbent (Dow DRYTECH 2035M) in a racetrack shape. |
| L | First absorbent layer with a basis weight of 200 gsm and containing 31% by weight superabsorbent (Stockhausen SXM-880) 9% bicomponent binder fiber, 60% Kraft pulp in a racetrack shape with a tensile strength of about 25 to 27N/50 mm and vertically above the second absorbent layer with a basis weight of 385 gsm and containing 50% ND-416 and 50% superabsorbent (Dow DRYTECH 2035M) in a rectangle shape |
| N | First absorbent layer with a basis weight of 100 gsm and containing 17% bicomponent binder fiber, 3% latex binder, 80% Kraft pulp in a racetrack shape with a tensile strength of 26 N/50 mm and vertically above the second absorbent layer with a basis weight of 545 gsm containing 50% ND-416 and 50% superabsorbent (Dow DRYTECH 2035M) in a rectangle shape. |

At the end of the interviews after the product use period, several prototypes were placed on the table for the panelist to view. Each panelist was to select the prototype that they would most likely choose to wear overall based on their recent use of the products. They also chose one prototype each that they felt would be the most absorbent, most comfortable, and most secure to wear based on perceptions only (they were not allowed to touch the pads). Two pads were also chosen as the ones that they would not even consider wearing.

Detailed descriptions of the absorbent structure of each code and retention capacity results are shown in Table 5.

TABLE 5

| Code | Upper over Lower | SAP % | Fiber % | Density g/cc | Thickness mm | Ret. Cap. g |
|---|---|---|---|---|---|---|
| C | 448 gsm fluff/SAP | 43.5 | 56.5 | 0.12 | 3.73 | N/A |
| control | 306 gsm fluff/SAP | 10.0 | 90.0 | 0.16 | 1.91 | N/A |
| | Total | | | | 5.64 | 97 |
| | Upper layer is rectangle | | | | | |
| R | 200 gsm bonded airlaid | 31 | 69 | 0.193 | 1.04 | N/A |
| | 290 gsm (ND-416) fluff/SAP | 50 | 50 | 0.30 | 0.97 | N/A |
| | Total | | | | 2.01 | 107 |
| | Upper layer is rectangle | | | | | |
| L | 200 gsm bonded airlaid | 31 | 69 | 0.193 | 1.04 | N/A |
| | 385 gsm(ND-416) fluff/SAP | 50 | 50 | 0.30 | 1.28 | N/A |
| | Total | | | | 2.32 | 93 |
| | Lower layer is rectangle | | | | | |
| N | 100 gsm bonded airlaid | 0 | 100 | 0.082 | 1.2 | N/A |
| | 545 gsm(ND-416) fluff/SAP | 50 | 50 | 0.30 | 1.81 | N/A |
| | Total | | | | 3.02 | 86 |
| | Lower layer is rectangle | | | | | |

Note 1:
Composition of 200 gsm bonded airlaid materials in Table 13:
31% by weight Stockhausen SXM-880 superabsorbent
9% bicomponent binder fiber (Trevira Type T255 3 mm 2 denier binder fiber)
60% Kraft pulp
Tensile strength is about 25 to 27 Newtons/50 mm
Made by Concert Industries
Note 2:
Composition of 100 gsm bonded airlaid material in Table 13:
17% by weight bicomponent binder fiber
3% by weight latex binder
80% Kraft pulp
Tensile strength was 26 Newtons/50 mm
Note 3:
SAP for Code C is Stockhausen SXM-880, pulp is Weyerhaeuser NB-416.
Note 4:
SAP for lower layers with ND-416 pulp is Dow 2035M.

The control code C is made from conventional low-density fluff/SAP absorbent materials. It is much thicker than all the other codes. In addition, each of the codes, except N, is close to a 100 g capacity. Code R has a relatively small rectangular upper layer made from bonded airlaid material. Codes L and N have larger airlaid upper layers and the lower layer is a rectangle shape underneath the upper stabilized layer.

Qualitatively, there appeared to be no differences in leakage performance among the codes. This was the desired result for the very thin pads. Most people (10 of 13) liked the thin codes R, L, and N more than the control. Thinness, discretion, and lack of bunching and distortion in use were primary reasons. Code N, with no superabsorbent in the upper layer, seems to "mask" urine color in used product compared to the control and the other codes. Code R, with the large lower layer, tended to bunch more than codes N and L. but less than the control. This suggests a larger stabilized upper layer over a smaller area lower bonded layer (codes N and L) is advantageous. The study results also suggest that all three prototypes, N, L, R, of the current invention are improvements over the control product.

Example 6

The products of Example 5 were also subjected to a multiple insult fluid intake test. Table 6 shows the results.

The multiple insult intake test is used to measure the fluid intake time and flowback of adult incontinence pads. The fluid intake time is measured by using a timing device and visually estimating the length of time required to absorb three individual fluid insults. The fluid is 0.9% by weight sodium chloride dissolved in deionized water along with about 0.004 g/liter FD&C Blue #1 dye to make the liquid more visible. The test is typically done at room temperature (about 21° C.). Layers of blotting paper are provided under the specimen (an incontinence pad) to collect any testing fluid that may flow over the side of the specimen. Apparatus for conducting this test include a four ounce capacity funnel part number 06122-20 available from Cole-Parmer Instrument Company (www.coleparmer.com) or equivalent. Additionally, a test board (essentially a cylinder with a 25.4 mm inside diameter mounted on a plexiglass plate that fits on top of a mounting board and the test sample is mounted between the plate and the board) available from Kimberly-Clark Corporation is required, a stopwatch, and a pump or beaker to pour the liquid into the cylinder. For small samples, as used in Table 6, the liquid was poured into the test board cylinder tube by hand. The sample is placed in the test board and secured (by pressing) on the board to insure a secure seal. A five ml insult was poured into the tube and the stopwatch started. As soon as the fluid was totally absorbed (visual observation), the time was recorded. After one minute, the procedure was repeated for the second insult. After another minute, the procedure was repeated for a third 5 ml insult. Five samples were tested for each code and the results appear in Table 6. A longer time means it takes that sample longer to absorb a fluid insult. Typically, lower times are better because the product tested will be less likely to leak in use.

TABLE 6

|  | Code C | Code R | Code N | Code L |
|---|---|---|---|---|
| Insult #1 | Avg. 2.1 | Avg. 2.7 | Avg. 2.0 | Avg. 2.7 |
|  | StDv. 0.1 | StDv. 0.3 | StDv. 0.2 | StDv. 0.3 |
| Insult #2 | Avg. 6.8 | Avg. 4.1 | Avg. 3.0 | Avg. 4.3 |
|  | StDv. 1.5 | StDv. 0.5 | StDv. 0.4 | StDv. 0.5 |
| Insult #3 | Avg. 11.2 | Avg. 4.7 | Avg. 3.5 | Avg. 5.0 |
|  | StDv. 2.5 | StDv. 0.4 | StDv. 0.3 | StDv. 0.9 |

Note:
All times are in seconds.

The results for the first insult show very similar intake times for all three codes, indicating that for a single 5 ml insult, they should all work about the same. For the second insult, Code C, begins to take longer to absorb liquid and for the third insult it takes much longer for Code C to absorb the liquid. Thus, the results of this testing suggest that the combination of the stabilized first absorbent and the high density second absorbent in codes R, N, and L provide superior fluid intake for multiple liquid insult situations along with the other advantages described before.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed:

1. An absorbent core for use in an absorbent article comprising:
  a. a stabilized first absorbent layer; and,
  b. a second absorbent layer adjacent the first absorbent layer and including (i) absorbent fibers treated with a non-fugitive densification agent and (ii) a superabsorbent material.

2. The absorbent core of claim 1 wherein the first absorbent layer comprises absorbent fibers.

3. The absorbent core of claim 1 wherein the first absorbent layer comprises a superabsorbent.

4. The absorbent core of claim 1 wherein the second absorbent layer has a greater density than the first absorbent layer.

5. The absorbent core of claim 1 wherein in use the first absorbent layer is vertically above the second absorbent layer.

6. The absorbent core of claim 1 wherein in use the first absorbent layer is vertically below the second absorbent layer.

7. The absorbent core of claim 1 wherein the first absorbent layer is a stabilized airlaid absorbent.

8. The absorbent core of claim 7 wherein the first absorbent layer contains from 0 to about 60% superabsorbent.

9. The absorbent core of claim 1 wherein the second absorbent layer has a density of at least about 0.15 g/cc.

10. The absorbent core of claim 1 wherein the second absorbent layer has a density of at least about 0.3 g/cc.

11. The absorbent core of claim 1 wherein non-fugitive densification agent forms hydrogen bonds and is selected from the group consisting of polymeric densification agents, non-polymeric densification agents, and mixtures thereof.

12. The absorbent core of claim 1 wherein non-fugitive densification agent is a high boiling point hydrogen bonding agent.

13. The absorbent core of claim 12 wherein the non-fugitive densification agent is selected from the group consisting of propylene glycol, glycerin, and mixtures thereof.

14. The absorbent core of claim 12 wherein the non-fugitive densification agent is a polymer having a molecular weight between about 4,000 and about 8,000 gm/mole.

15. The absorbent core of claim of claim 12 wherein the non-fugitive densification agent is a polymer having a molecular weight greater than about 8,000 gm/mole.

16. The absorbent core of claim 1 wherein the second absorbent layer contains from about 10% to about 75% superabsorbent.

17. The absorbent core of claim 1 wherein the first absorbent layer and the second absorbent layer have a combined thickness of about 5 millimeters or less.

18. The absorbent core of claim 1 wherein the first absorbent and the second absorbent have a combined thickness of about 2 millimeters or less.

19. The absorbent core of claim 1 wherein the first absorbent layer has a tensile strength of at least about 6 N/50 mm.

20. The absorbent core of claim 19 wherein the first absorbent layer in a dry state has a tensile strength of about 6 N/50 mm.

21. The absorbent core of claim 20 wherein the first absorbent layer in a wet state has a tensile strength of at least about 2 N/50 mm.

22. The absorbent core of claim 19 wherein the second absorbent layer in a dry state has a tensile strength of about 0.5 N/50 mm.

23. An absorbent core for use in an absorbent article comprising:
  a. a stabilized first air formed absorbent layer including absorbent fibers such that the first absorbent layer in a dry state has a tensile strength of at least about 6 N/50 mm and in a wet state has a tensile strength of at least about 2 N/50 mm; and,
  b. a second absorbent layer adjacent the first absorbent layer and including (i) absorbent fibers treated with a non-fugitive densification agent and (ii) a superabsorbent material wherein the non-fugitive densification agent forms hydrogen bonds and is selected from the group consisting of polymeric densification agents, non-polymeric densification agents, and mixtures thereof.

24. The absorbent core of claim 23 wherein the second absorbent layer has a density greater than a density of the first absorbent layer.

25. The absorbent core of claim 23 wherein the non-fugitive densification agent is selected from the group consisting of propylene glycol, glycerin, and mixtures thereof.

26. The absorbent core of claim 23 wherein the second absorbent layer contains from about 10% to about 75% superabsorbent.

27. The absorbent core of claim 23 wherein the first absorbent layer and the second absorbent layer have a combined thickness of about 5 millimeters or less.

28. The absorbent core of claim 23 wherein in use the first absorbent layer is vertically above the second absorbent layer.

29. The absorbent core of claim 23 wherein in use the first absorbent layer is vertically below the second absorbent layer.

30. An absorbent article comprising:
  a. a liner;
  b. a baffle;
  c. a stabilized first absorbent layer; and,
  d. a second absorbent layer adjacent the first absorbent layer and including a superabsorbent material and absorbent fibers treated with a non-fugitive densification agent.

31. The absorbent article of claim 30 wherein the first absorbent layer is vertically below a first side of the liner and the second absorbent layer is vertically below the first absorbent layer.

32. The absorbent article of claim 30 wherein the second absorbent layer is vertically below a first side of the liner and the first absorbent layer is vertically below the second absorbent layer.

33. The absorbent article of claim 30 wherein the first absorbent layer comprises absorbent fibers.

34. The absorbent article of claim 33 wherein the non-fugitive densification agent forms hydrogen bonds and is selected from the group consisting of polymeric densification agents, non-polymeric densification agents, and mixtures thereof.

35. The absorbent article of claim 33 wherein the non-fugitive densification agent is a high boiling point hydrogen bonding agent.

36. The absorbent article of claim 33 wherein the non-fugitive densification agent is selected from the group consisting of propylene glycol, glycerin, and mixtures thereof.

37. The absorbent article of claim 36 wherein the second absorbent layer has a greater density than the first absorbent layer.

38. The absorbent article of claim 36 wherein the second absorbent layer has a density of at least 0.15 g/cc.

39. The absorbent article of claim 36 wherein the second absorbent layer has a density of at least 0.3 g/cc.

40. The absorbent article of claim 30 wherein the second absorbent layer contains from about 10% to about 75% superabsorbent.

41. The absorbent article of claim 30 wherein the first absorbent layer and the second absorbent layer have a combined thickness of about 5 millimeters or less.

42. A process for making an absorbent core comprising:
   a. providing a first absorbent material;
   b. providing a second material that includes (i) absorbent fibers treated with a non-fugitive densification agent and (ii) a superabsorbent material;
   c. cutting the first absorbent material to form a first absorbent layer;
   d. placing the first absorbent layer adjacent the second absorbent material; and,
   e. cutting the second material to form a second absorbent material to form an absorbent core.

43. The process of claim 42 further comprising:
   a. providing a liner; and
   b. providing a baffle such that the absorbent core is disposed between the liner and the baffle.

44. The process of claim 43 wherein the absorbent core is disposed such that the liner is adjacent the first absorbent layer.

* * * * *